(12) United States Patent
Endo et al.

(10) Patent No.: US 9,597,674 B2
(45) Date of Patent: Mar. 21, 2017

(54) Z-SELECTIVE OLEFIN METATHESIS CATALYSTS AND THEIR SYNTHETIC PROCEDURE

(75) Inventors: Koji Endo, Chiba (JP); Benjamin Keith Keitz, Pasadena, CA (US); Myles Benton Herbert, Pasadena, CA (US); Paresma Rasiklal Patel, Los Angeles, CA (US); Robert Howard Grubbs, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 382 days.

(21) Appl. No.: 13/978,940

(22) PCT Filed: Jan. 17, 2012

(86) PCT No.: PCT/US2012/021609
§ 371 (c)(1),
(2), (4) Date: Jan. 6, 2014

(87) PCT Pub. No.: WO2012/097379
PCT Pub. Date: Jul. 19, 2012

(65) Prior Publication Data
US 2014/0106960 A1   Apr. 17, 2014

Related U.S. Application Data

(60) Provisional application No. 61/432,849, filed on Jan. 14, 2011, provisional application No. 61/433,949, (Continued)

(51) Int. Cl.
*B01J 31/22* (2006.01)
*C07C 6/04* (2006.01)
(Continued)

(52) U.S. Cl.
CPC ....... *B01J 31/2295* (2013.01); *B01J 31/2208* (2013.01); *B01J 31/2273* (2013.01);
(Continued)

(58) Field of Classification Search
None
See application file for complete search history.

(56) References Cited

U.S. PATENT DOCUMENTS 5,312,940 A   5/1994   Grubbs et al.
6,284,852 B1  9/2001   Lynn et al.
(Continued)

FOREIGN PATENT DOCUMENTS

EP   2255877 A1    12/2010
JP   2002516911 A   6/2002
(Continued)

OTHER PUBLICATIONS

Keitz et al. JACS, 2012, 134, 693.*
(Continued)

*Primary Examiner* — Yun Qian
(74) *Attorney, Agent, or Firm* — J.A. Lindeman & Co., PLLC

(57) ABSTRACT

The invention relates to C—H activated olefin metathesis catalyst compounds, the preparation of such compounds, and the use of such catalysts in the metathesis of olefins and olefin compounds, more particularly, the use of such catalysts in Z selective olefin metathesis reactions. In general, the catalyst compounds of the invention comprise a Group 8 metal (M), an alkylidene moiety ($=CR^1R^2$), or more generally ($=(C)_mCR^1R^2$), an anionic ligand ($X^1$), two or three neutral ligands ($L^1$, $L^2$, and $L^3$) and a 2-electron anionic donor bridging moiety ($Q^*$) that forms a chelate ring structure in conjunction with L1 and M. Such catalysts generally correspond to the formula $X^1(L^3)_kL^2L^1Q^*M=(C)$
(Continued)

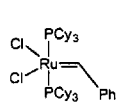

1

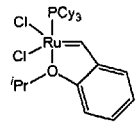

2

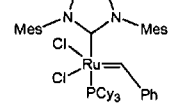

3

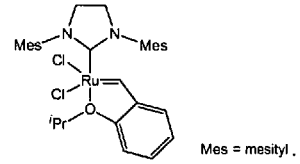

4

Typical Grubbs' Catalysts $_m$CR$^1$R$^2$, wherein X1 is any anionic ligand, L$^1$, L$^2$, and L$^3$ are, independently, any neural electron donor ligand, k is 0 or 1, m is 0, 1, or 2, Q* is a 2-electron anionic donor bridging moiety linking L$^1$ and M, M is a Group 8 transition metal, and R$^1$ and R$^2$ are, independently, hydrogen, hydrocarbyl, substituted hydrocarbyl, heteroatom-containing hydrocarbyl, substituted heteroatom-containing hydrocarbyl, or functional groups. The invention has utility in the fields of catalysis, organic synthesis, polymer chemistry, and industrial and fine chemicals chemistry.

4 Claims, 6 Drawing Sheets

Related U.S. Application Data filed on Jan. 18, 2011, provisional application No. 61/515,262, filed on Aug. 4, 2011.

(51) Int. Cl.
 C07F 15/00 (2006.01)
 C07C 67/343 (2006.01)
(52) U.S. Cl.
 CPC ............ *B01J 31/2278* (2013.01); *C07C 6/04* (2013.01); *C07C 67/343* (2013.01); *C07F 15/0046* (2013.01); *B01J 31/223* (2013.01); *B01J 31/2226* (2013.01); *B01J 2231/543* (2013.01); *B01J 2531/0261* (2013.01); *B01J 2531/821* (2013.01); *C07C 2531/22* (2013.01); *Y02P 20/52* (2015.11)

(56) References Cited

U.S. PATENT DOCUMENTS

| | | | |
|---|---|---|---|
| 6,620,955 | B1 | 9/2003 | Pederson et al. |
| 6,921,735 | B2 | 7/2005 | Hoveyda et al. |
| 7,026,495 | B1 | 4/2006 | Pederson et al. |
| 7,678,932 | B2 | 3/2010 | Thurier et al. |
| 2003/0236427 | A1 | 12/2003 | Grubbs et al. |
| 2006/0128912 | A1 | 6/2006 | Piers et al. |
| 2007/0043180 | A1 | 2/2007 | Zhan |
| 2011/0124868 | A1* | 5/2011 | Grubbs ............... C07C 67/333 546/4 |

FOREIGN PATENT DOCUMENTS

| | | |
|---|---|---|
| JP | 2006143734 A | 6/2006 |
| WO | 02/14376 A2 | 2/2002 |

OTHER PUBLICATIONS

Grubbs et al. (JACS, 2006, 128, 11768-11769).*
Jazzar et al., J. Am. Chem. Soc. 124(18):4944-4945 (2002).
Samojlowicz et al., Chem. Rev. 109(8):3708-3742 (2009).
Burling et al., Organometallics 28(23):6676-6686 (2009).
International Search Report of PCT International Application No. PCT/US2012/021609, dated Aug. 22, 2012.
Extended European Search Report in Application No. 12734668.2 dated Jun. 20, 2014.
K. Endo et al.: "Chelated Ruthenium Catalysts for Z-Selective Olefin Metathesis," Journal of the American Chemical Society, vol. 133, pp. 8525-8257, May 12, 2011.
D. Gusev et al.: "Alkylidene and Vinylidene "Pincer" Complexes from Reactions of Alkynes with Ruthenium and Osmium Hydrides," Organometallics, vol. 21, pp. 1095-1100, 2002.
B. Keitz et al.: "Z-Selective Homodimerization of Terminal Olefins with a Ruthenium Metathesis Catalyst," Journal of the American Chemical Society, vol. 133, pp. 9686-9688, Jun. 8, 2011.
B. Keitz et al.: "Improved Ruthenium Catalysts for Z-Selective Olefin Metathesis," Journal of the American Chemical Society, vol. 134, pp. 693-699, Nov. 19, 2011.
B. Keitz et al.: "Cis-Selective Ring-Opening Metathesis Polymerization with Ruthenium Catalysts," Journal of the American Chemical Society, vol. 134, pp. 2040-2043, Jan. 12, 2012.
V. Kuznetsov et al.: "Triple C-H Activation of 1,5-bis(di-tert-butylphosphino)-2-(S)-dimethylaminopentane on Ruthenium Gives a Chiral Carbene Complex," Chem. Comm., pp. 2432-2433, Sep. 24, 2002.
T. Wen et al.: "Osmium-Mediated Hexamerization of Phenylacetylene," Agnew. Chem. Int. Ed., vol. 45, pp. 5842-5846, 2006.
T. Wen et al.: "Coupling Reaction of Phyenylacetylene with OsHn(PPH3)(2,6-(PPh2CH2)2C6H3)(n=1,3)." Organometallics, vol. 22, pp. 4947-4951, 2003.
PCT International Preliminary Report on Patentability for PCT International Application No. PCT/US2012/021609, dated Jul. 16, 2013.
Chatterjee et al., "A General Model for Selectivity in Olefin Cross Metathesis," J. Am. Chem. Soc. 125:11360-11370 (2003).
Jafarpour et al., "Improved One-Pot Synthesis of Second-Generation Ruthenium Olefin Metathesis Catalysts," Organometallics 21:442-444 (2002).
Flook et al., "Z-Selective Olefin Metathesis Processes Catalyzed by a Molybdenum Hexaisopropylterphenoxide Monopyrrolide Complex," J. Am. Chem. Soc. 131:7962-7963 (2009).
Krause et al., "Synthesis and Reactivity of Homogeneous and Heterogeneous Ruthenium-Based Metathesis Catalysts Containing Electron-Withdrawing Ligands," Chem. Eur. J. 10:777-784 (2004).
Paczal et al., "Modular Synthesis of Heterocyclic Carbene Precursors," J. Org. Chem. 71:5969-5979 (2006).
Pangborn et al., "Safe and Convenient Procedure for Solvent Purification," Organometallics 15:1518-1520 (1996).
Rosen et al., "Olefin Metathesis Catalysts Containing Acyclic Diaminocarbenes," Organometallics 29:250-256 (2010).
Teo et al., "Facile Synthesis of Efficient and Selective Ruthenium Olefin Metathesis Catalysts with Sulfonate and Phosphate Ligands," Organometallics 29:6045-6050 (2010).
Elschenbroich in "Organometallics" (1989 VCH p. 439).
Goldman and Goldberg in "Organometallic C-H Bond Activation: An Introduction," pp. 1-43 (Jul. 12, 2004, American Chemical Society).
Janowicz et al., J. Am. Chem. Soc. 1982, 104, 352-354.

* cited by examiner

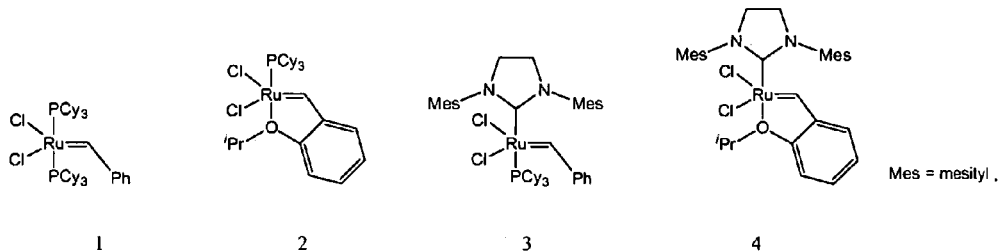
Figure 1. Typical Grubbs' Catalysts
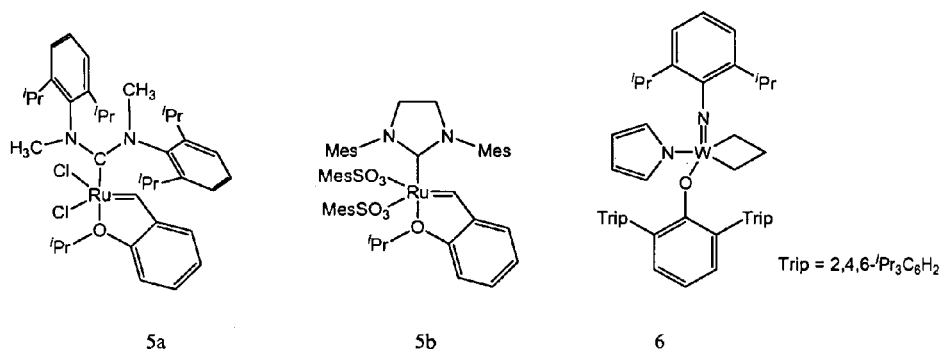
Figure 2. Recently Reported Olefin Metathesis Catalysts
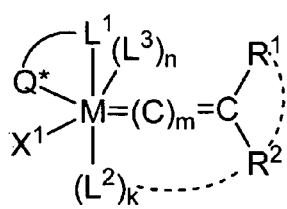
Figure 3. General structure of Z selective olefin metathesis catalyst

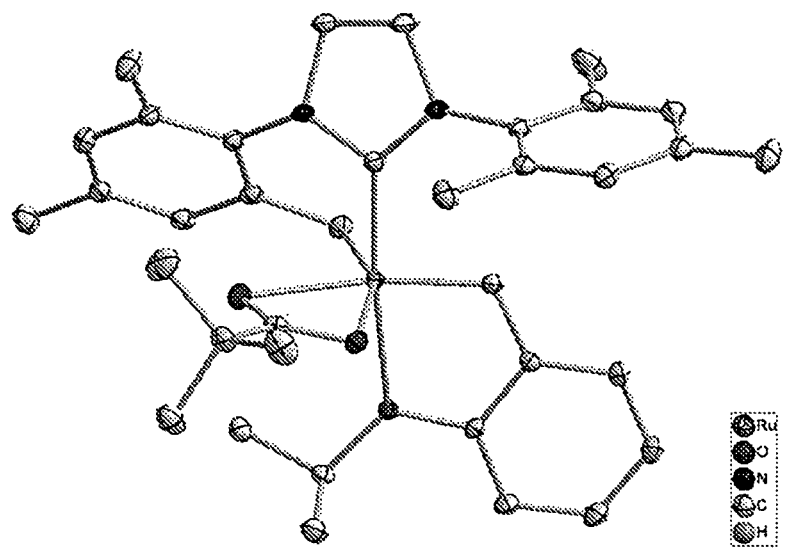
Figure 4. X-ray crystal structure of complex 7a
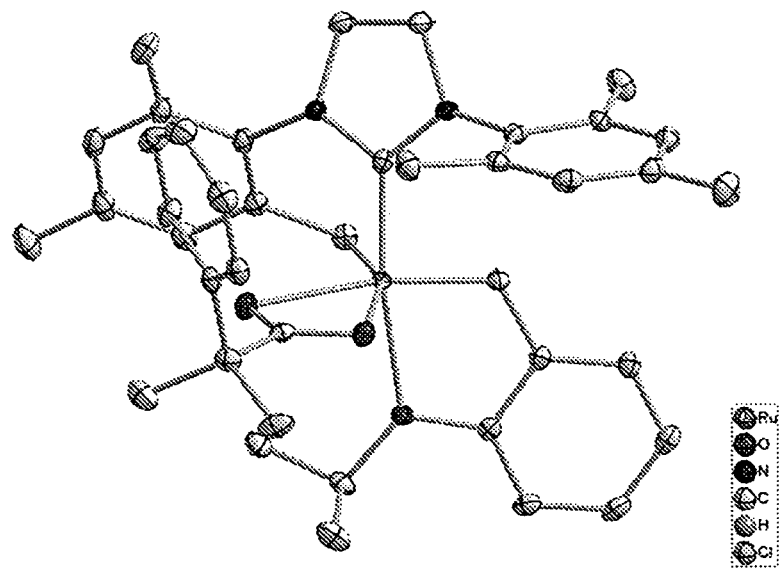
Figure 5. X-ray crystal structure of complex 7b

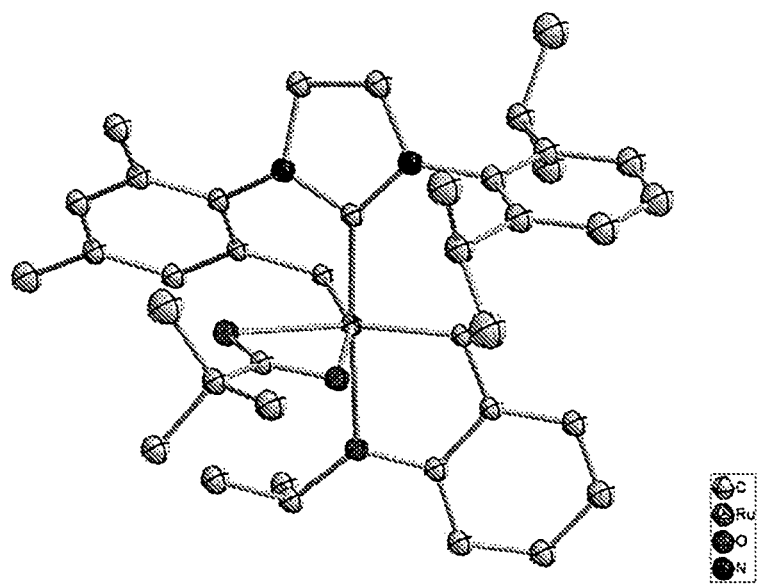
Figure 6. X-ray crystal structure of complex 11
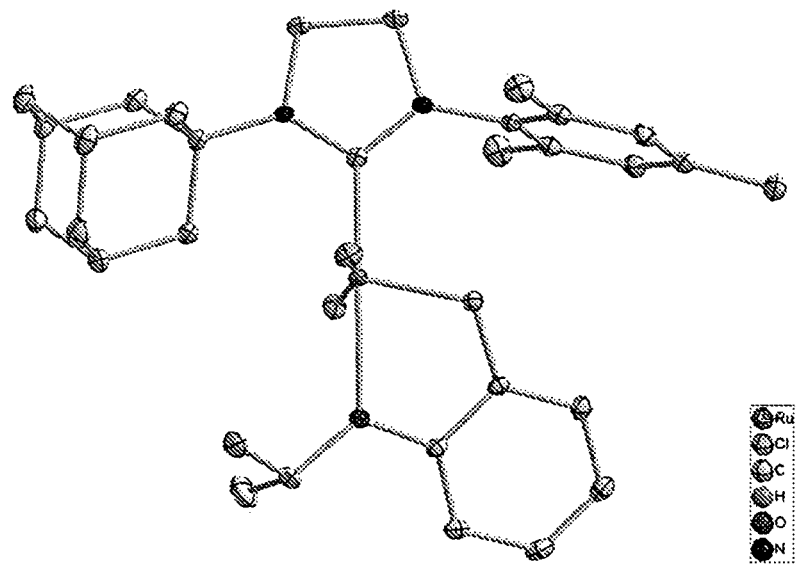
Figure 7. X-ray crystal structure of complex 18a

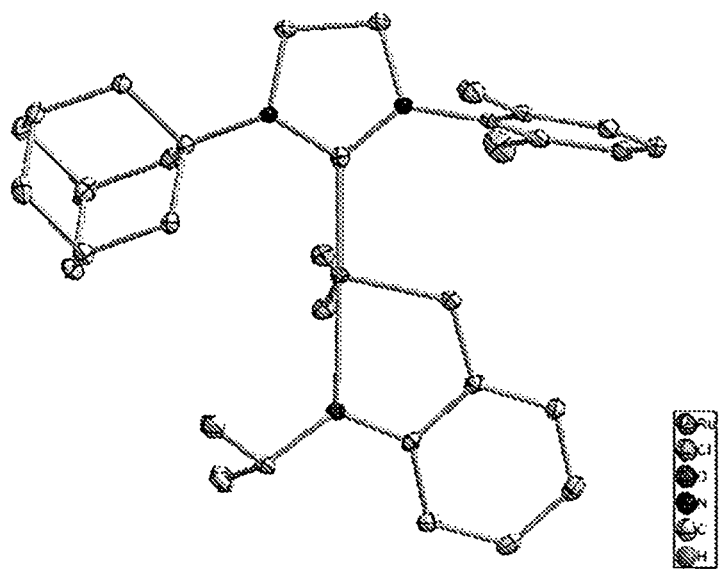
Figure 8. X-ray crystal structure of complex 18b
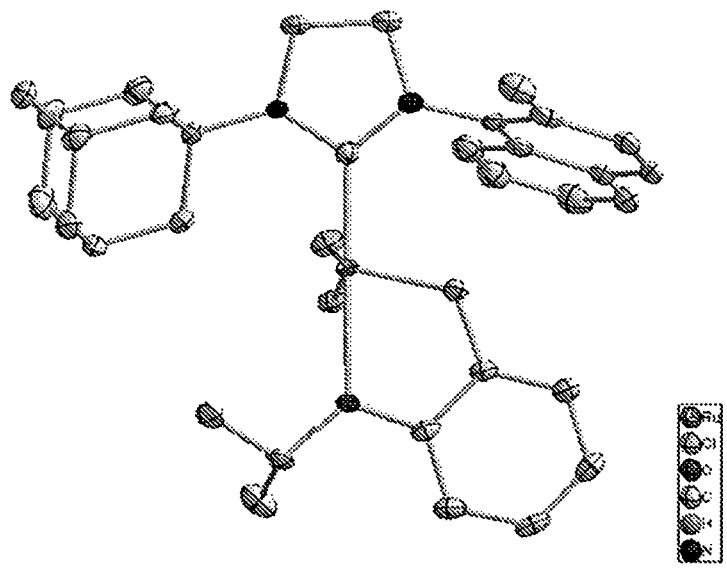
Figure 9. X-ray crystal structure of complex 18c

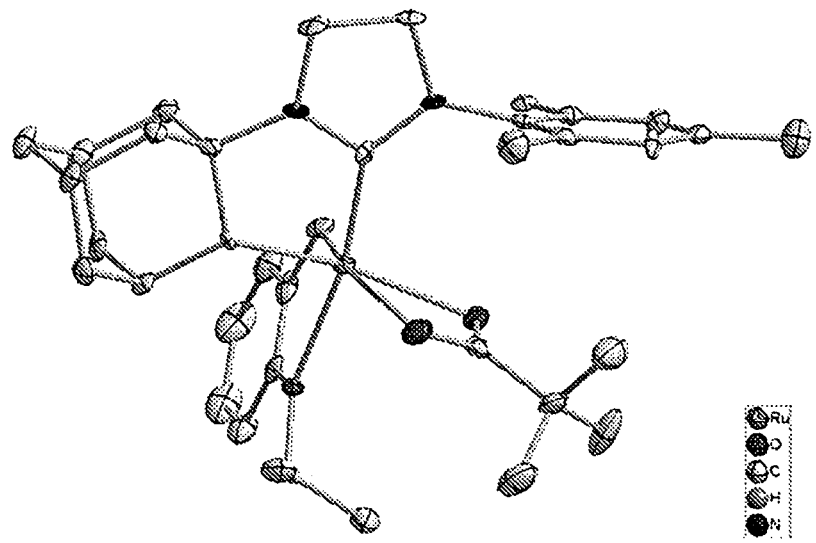
Figure 10. X-ray crystal structure of complex 19a
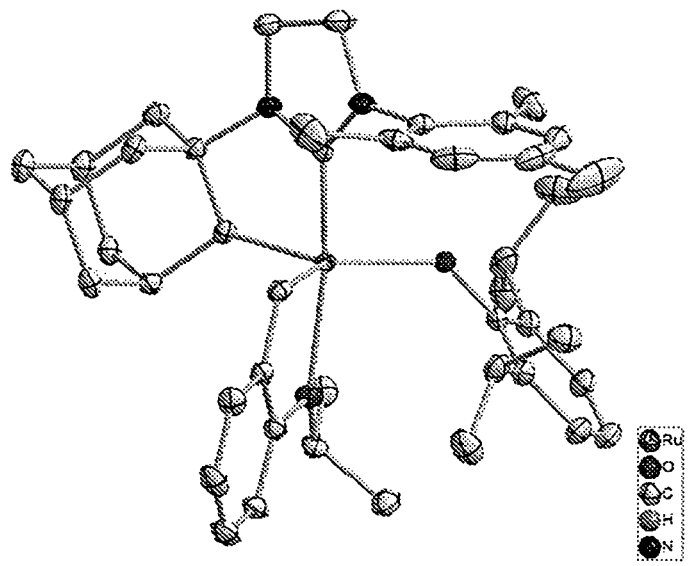
Figure 11. X-ray crystal structure of complex 21a

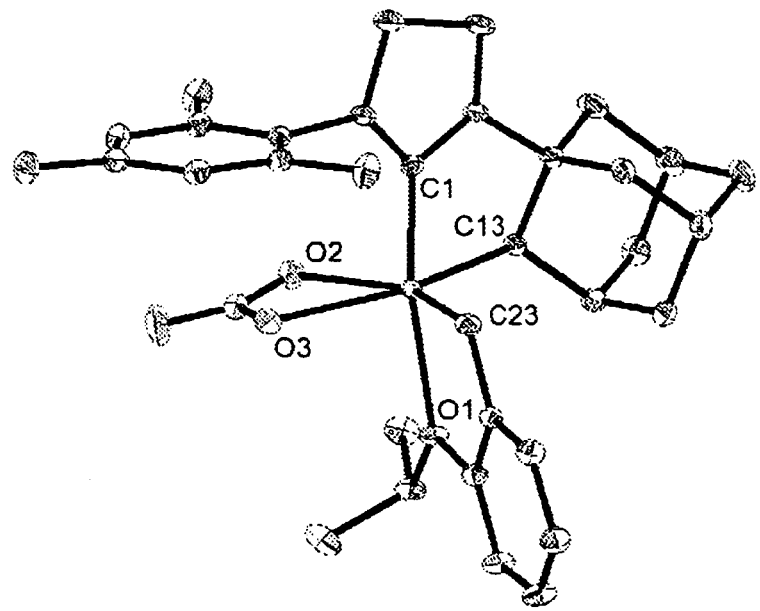
Figure 12. X-ray crystal structure of complex 22e
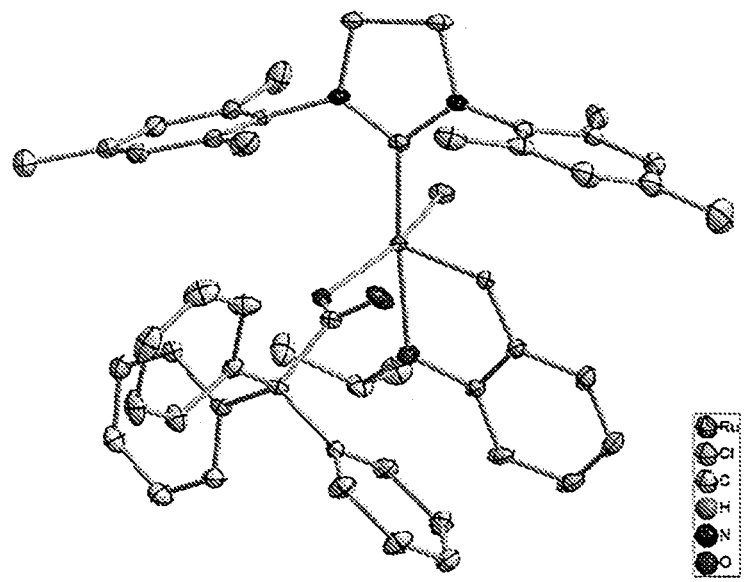
Figure 13. X-ray crystal structure of complex 24d

Z-SELECTIVE OLEFIN METATHESIS CATALYSTS AND THEIR SYNTHETIC PROCEDURE

RELATED APPLICATIONS

This application claims the benefit of priority to U.S. Provisional Application Ser. No. 61/432,849 (CIT-5776-P), filed Jan. 14, 2011, U.S. Provisional Application Ser. No. 61/433,949 (CIT-5776-P2), filed Jan. 18, 2011, and U.S. Provisional Application Ser. No. 61/515,262 (CIT-5776-P3), filed Aug. 4, 2011, each of which is incorporated herein by reference.

STATEMENT REGARDING FEDERALLY SPONSORED RESEARCH OR DEVELOPMENT

This invention was made with government support under Grant No. GM031332 awarded by the National Institutes of Health and under Grant No. CHE1048404 awarded by the National Science Foundation. The government has certain rights in the invention.

TECHNICAL FIELD

This invention relates generally to C—H activated olefin metathesis catalyst compounds, to the preparation of such compounds, and the use of such catalysts in the metathesis of olefins and olefin compounds, more particularly, in the use of such catalysts in Z selective olefin metathesis reactions. The invention has utility in the fields of catalysis, organic synthesis, polymer chemistry, and industrial and fine chemicals chemistry.

BACKGROUND

Since its discovery in the 1950s, olefin metathesis has emerged as a valuable synthetic method for the formation of carbon-carbon double bonds. In particular, its recent advances in applications to organic syntheses and polymer syntheses mostly rely on developments of well-defined catalysts. Among attempts to improve catalyst efficiency over the past decade, one of the most attractive frontiers has been selective synthesis of stereo-controlled olefin product. Derived from generally accepted their equilibrium reaction mechanisms, most of catalysts give higher proportion of thermodynamically favored E isomer of olefin in products. This fundamental nature of olefin metathesis limits its applications to some reactions including natural product synthesis. Thus, a catalyst which selectively gives Z isomer of olefin product is expected to open a new convenient route to a value-added product. Especially, use of Z selective catalysts in olefin cross metathesis (CM) is promising for outstanding methodology in organic chemistry. In the simplest case of such CM, two different terminal olefin molecules selectively generate one new internal cis-olefin molecule and one ethylene molecule (Scheme 1).

One of the most important classes of olefin metathesis catalysts is ruthenium-based alkylidene complex represented by the ruthenium catalyst (1-4) (FIG. 1). Because of their high efficiency in catalysis and high tolerance towards various functional groups, they are most widely used in both academic and industrial fields. Typical ruthenium catalysts are known to give more E isomer than Z isomer in CM and other olefin metathesis reactions (see Chatterjee, A. K.; Choi, T.-L.; Sanders, D. P.; Grubbs, R. H. *J. Am. Chem. Soc.* 2003, 125, 11360).

Bielawski et al. reported that a ruthenium catalyst having acyclic diaminocarbene ligand (5) afforded the cross coupled product in a nearly 1:1 ratio of its E and Z isomers at high conversion (~75%) in CM of allylbenzene and cis-1,4-diacetoxy-2-butene (see Rosen, E. L.; Sung, D. H.; Chen, Z.; Lynch, V. M.; Bielawski, C. W. *Organometallics* 2010, 29, 250). Grubbs et al. also demonstrated that a bulky sulfonate ligand substituted 2nd generation catalyst (6), which was readily prepared from commercially available reagents, gave the product with E isomer/Z isomer=2.9 at very high conversion (~90%) in the same CM reaction (see Teo, P.; Grubbs, R. H. *Organometallics* 2010, 29, 6045). Compared to the original ruthenium catalysts, these catalysts gave much more Z isomer of the product; however, their Z selectivity were still not satisfactory for precisely stereo-controlled reactions. On the other hand, some of the molybdenum- or tungsten-based catalysts recently developed by Hoveyda and Schrock are outstanding for their Z selectivity in metathesis homocoupling of terminal olefins (see Jiang, A. J.; Zhao, Y.; Schrock, R. R.; Hoveyda, A. H. *J. Am. Chem. Soc.* 2009, 131, 7962). In a particular case, bulky aryloxide substituted tungsten catalyst (7) afforded homocoupled product of 1-hexene with 95% Z isomer. Despite the excellent Z selectivity, their relatively many synthetic steps and generally required strict reaction conditions for molybdenum and tungsten alkylidene catalysts somewhat restrict their use in common organic syntheses.

In order to overcome the above mentioned disadvantages of the current catalysts, new highly Z selective ruthenium based catalysts are needed. For general use, especially in industry, they should be not only tolerant towards various functional groups and impurities in reaction media but also readily synthesized from common reagents in simple reaction steps. Despite the advances achieved in preparing olefin metathesis catalysts, a continuing need in the art exists for improved catalysts, including catalysts that provide improved Z selectivity.

BRIEF SUMMARY OF THE DISCLOSURE

The invention is directed to addressing one or more of the aforementioned concerns, and, in one embodiment, provides a C—H activated catalyst compound composed of a Group 8 transition metal complex and a chelating ligand structure formed from the metal center M, a neutral electron donor ligand $L^1$, and a 2-electron anionic donor bridging moiety, $Q^*$. A general structure of catalyst compounds according to the invention is shown below.

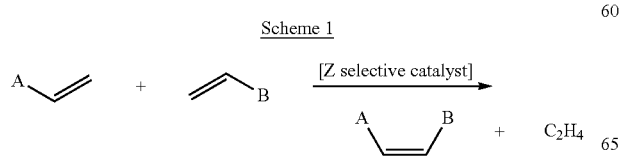

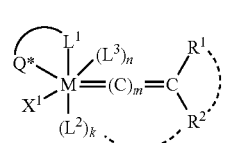

wherein, M is a Group 8 transition metal (e.g., Ru or Os); $X^1$ is any anionic ligand (e.g., halogen, alkyl, aryl, carboxylate, alkoxy, aryloxy, sulfonate, phosphate, or nitrate); $L^1$, $L^2$, and $L^3$ are, independently, any neutral two electron ligand, where $L^2$ may connect with $R^2$; $R^1$ and $R^2$ are independently selected from hydrogen, hydrocarbyl, substituted hydrocarbyl, heteroatom-containing hydrocarbyl, substituted heteroatom-containing hydrocarbyl, and functional groups, and wherein $R^1$ may connect with $R^2$ and/or $L^2$; Q* is a 2-electron anionic donor bridging moiety, (e.g., alkyl, aryl, carboxylate, alkoxy, aryloxy, or sulfonate, etc.); n and k are independently 0 or 1, such that $L^3$ may or may not be present; and, m is 0, 1, or 2.

These complexes comprise a Group 8 metal (M), an alkylidene moiety ($=CR^1R^2$), an anionic ligand ($X^1$), two or three neutral ligands ($L^1$, $L^2$, and $L^3$) and a 2-electron anionic donor bridging moiety (Q*) which forms a chelate structure in conjunction with $L^1$ and M. As with other known active ruthenium catalysts (e.g., typical Grubbs' catalysts 1-4 of FIG. 1), these group 8 metal-based alkylidene catalysts of the invention are intrinsically tolerant towards various functional groups and impurities in reaction media. Advantageously, the C—H activated catalyst compounds of the invention may be used to catalyze Z selection olefin metathesis reactions.

In order to synthesize the chelated catalyst compounds of the invention, the following synthetic procedure can be utilized (Scheme 2). In the first step, two anionic ligands ($X^1$) of Grubbs' 2nd generation type complex are substituted by another anionic ligand ($X^2$), by contacting the catalyst complex with $M^1X^2$. Intramolecular C—H bond activation at the substituent of NHC ligand ($R^3$) and liberation of acid ($HX^2$) thereafter yield the chelated catalyst of the invention. As shown in scheme 3, an anionic ligand of the chelated catalyst ($X^1$) can be substituted by another anionic ligand ($X^2$) by reaction with corresponding Lewis base. For example, in one aspect of the invention, it has now been found that the addition of a nitrate ($NO_3^-$) group $X^2$ ligand in place of another $X^1$ anionic ligand provides catalysts according to the invention that demonstrate certain improvements in catalyzing olefin metathesis reactions.

It should be noted that a number of Grubbs' 2nd generation catalysts which can be precursors of the chelated catalysts in scheme 2 are now commercially available. In addition, most of reagents used for anion ligand exchange ($M^1X^2$) are also commercially available or readily prepared by simple reaction step(s). In this procedure $X^1$ and $X^2$ are different. Preferably $M^1X^1$ has lower solubility in the reaction media than $M^1X^2$.

Scheme 2. General Synthetic Procedure

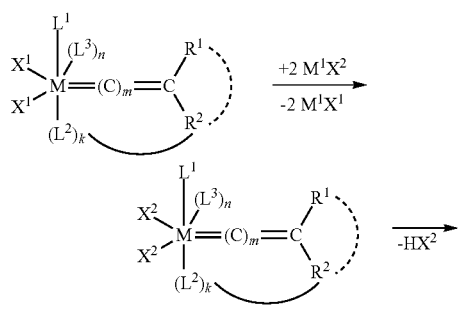

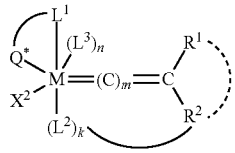

Scheme 3. Synthetic Procedure

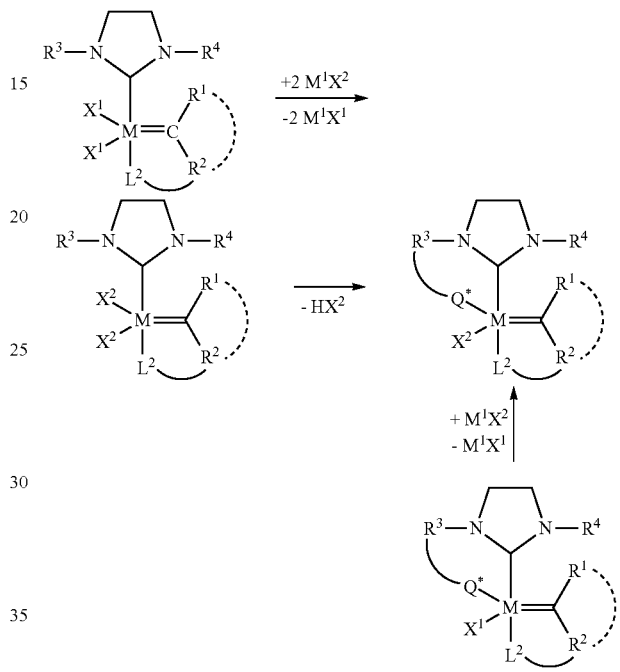

wherein, in each of Schemes 2 and 3, M is a Group 8 transition metal (e.g., Ru or Os); $M^1$ is a metal such as silver, lithium, sodium, potassium, rubidium, cesium, magnesium, calcium, strontium, barium, iron, zinc, or thalium; $X^1$ and $X^2$ are independently any anionic ligand (e.g., halogen, alkyl, aryl, carboxylate, alkoxy, aryloxy, sulfonate, phosphate, or nitrate); $L^1$, $L^2$, and $L^3$ are, independently, any neutral two electron ligand, where $L^2$ may connect with $R^2$; $R^1$ and $R^2$ are independently selected from hydrogen, hydrocarbyl, substituted hydrocarbyl, heteroatom-containing hydrocarbyl, substituted heteroatom-containing hydrocarbyl, and functional groups, and wherein $R^1$ may connect with $R^2$ and/or $L^2$; Q* is a 2-electron anionic donor bridging moiety, (e.g., alkyl, aryl, carboxylate, alkoxy, aryloxy, or sulfonate, etc.); n and k are independently 0 or 1, such that $L^3$ may or may not be present; and, m is 0, 1, or 2.

BRIEF DESCRIPTION OF THE DRAWINGS

FIG. 1 depicts selected typical Grubbs' catalysts.
FIG. 2 depicts some of the reported olefin metathesis catalysts.
FIG. 3 depicts the general structure of the inventive Z selective olefin metathesis catalyst compounds.
FIG. 4 depicts the X-ray crystal structure of complex 7a as described in the Examples.
FIG. 5 depicts the X-ray crystal structure of complex 7b as described in the Examples.

FIG. 6 depicts the X-ray crystal structure of complex 11 as described in the Examples.

FIG. 7 depicts the X-ray crystal structure of complex 18a as described in the Examples.

FIG. 8 depicts the X-ray crystal structure of complex 18b as described in the Examples.

FIG. 9 depicts the X-ray crystal structure of complex 18c as described in the Examples.

FIG. 10 depicts the X-ray crystal structure of complex 19a as described in the Examples.

FIG. 11 depicts the X-ray crystal structure of complex 21a as described in the Examples.

FIG. 12 depicts the X-ray crystal structure of complex 22a as described in the Examples.

FIG. 13 depicts the X-ray crystal structure of complex 24d as described in the Examples.

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, 1-butyl, octyl, decyl, and the like, as well as cycloalkyl groups such as cyclopentyl, cyclohcxyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of hetero-atom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR═NH where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R═hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R═hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl —SO$_2$—N(H) alkyl), $C_1$-$C_{24}$ dialkylaminosulfonyl —SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Catalyst Complexes

In general, the catalyst complexes of the invention comprise a Group 8 metal (M), an alkylidene moiety (=CR$^1$R$^2$), or more generally (=(C)$_m$CR$^1$R$^2$), an anionic ligand (X$^1$), two or three neutral ligands (L$^1$, L$^2$, and L$^3$), and a 2-electron anionic donor bridging moiety (Q*) that forms a chelate structure in conjunction with L$^1$ and M. Suitable catalysts generally have the formula (I)

wherein X$^1$ is any anionic ligand, L$^1$, L$^2$, and L$^3$ are, independently, any neural electron donor ligand, k is 0 or 1, m is 0, 1, or 2, Q* is a 2-electron anionic donor bridging moiety linking L$^1$ and M, M is a Group 8 transition metal, and R$^1$ and R$^2$ are, independently, hydrogen, hydrocarbyl, substituted hydrocarbyl, heteroatom-containing hydrocarbyl, substituted heteroatom-containing hydrocarbyl, or functional groups.

The olefin metathesis catalyst complex is preferably a Group 8 transition metal complex having the structure of formula (II)

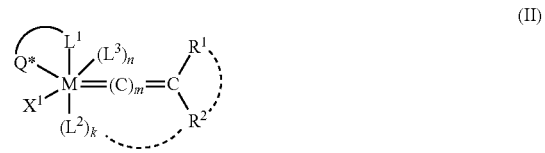

in which:
M is a Group 8 transition metal;
L$^1$, L$^2$ and L$^3$ are neutral electron donor ligands;
Q* is a 2-electron anionic donor bridging moiety linking L$^1$ and M, which can, together with L$^1$ and M, form one or more cyclic groups;
n is 0 or 1, such that L$^3$ may or may not be present;
m is 0, 1, or 2; k is 0 or 1;
X$^1$ is an anionic ligand; and
R$^1$ and R$^2$ are independently selected from hydrogen, hydrocarbyl, substituted hydrocarbyl, heteroatom-containing hydrocarbyl, substituted heteroatom-containing hydrocarbyl, and functional groups, wherein any two or more of X$^1$, Q*, L$^1$, L$^2$, L$^3$, R$^1$, and R$^2$ can be taken together to form one or more cyclic groups, and further wherein any one or more of X$^1$, Q*, L$^1$, L$^2$, L$^3$, R$^1$, and R$^2$ may be attached to a support. As shown in formula (II), L$^2$ may be optionally linked to R$^1$ or R$^2$, and R$^1$ may be optionally linked to R$^2$.

Preferred catalysts contain Ru or Os as the Group 8 transition metal, with Ru particularly preferred.

Catalysts according to formula (II) may be conveniently described according to certain structural features. In a first group of catalysts, commonly referred to as Second Generation Grubbs-type catalysts, L$^1$ in formula (II) is a carbene ligand having the structure of formula (III)

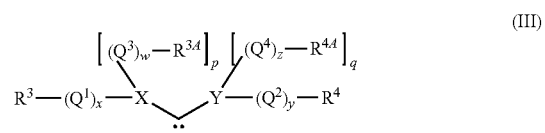

such that the complex may have the structure of formula (IV)

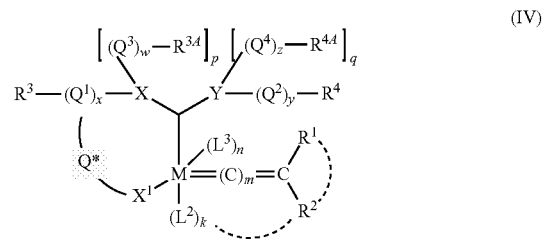

wherein M, m, n, X$^1$, L$^2$, L$^3$, R$^1$, and R$^2$ are as defined for the first group of catalysts, and the remaining substituents are as follows.

X and Y are heteroatoms typically selected from N, O, S, and P. Since O and S are divalent, p is necessarily zero when X is O or S, q is necessarily zero when Y is O or S, and k is zero or 1. However, when X is N or P, then p is 1, and when Y is N or P, then q is 1. In certain embodiments, both X and Y are N.

Q* is a 2-electron anionic donor bridging moiety linking and M, and may be hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Although not limited thereto, in one aspect, Q* may link $Q^1$ to M by a carbon-metal bond.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Although not limited thereto, in one aspect, $Q^1$ may be linked to M by Q* through a carbon-metal bond. Two or more substituents on adjacent atoms within $Q^1$, $Q^2$, $Q^3$, and $Q^4$ may also be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups.

$X^1$ is an anionic ligand, and, as described below, may be linked together to form a cyclic group, typically although not necessarily a five- to eight-membered ring. Typically, $X^1$ is hydrogen, halide, nitrate, or one of the following groups: $C_1$-$C_{20}$ alkyl, $C_5$-$C_{24}$ aryl, $C_1$-$C_{20}$ alkoxy, $C_1$-$C_{20}$ alkylcarboxylate, $C_5$-$C_{24}$ aryloxy, $C_2$-$C_{20}$ alkoxycarbonyl, $C_6$-$C_{24}$ aryloxycarbonyl, $C_6$-$C_{24}$ arylcarboxylate, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. $X^1$ may be optionally substituted with one or more moieties selected from $C_1$-$C_{12}$ alkyl, $C_1$-$C_{20}$ alkylcarboxylate, $C_1$-$C_{12}$ alkoxy, $C_5$-$C_{24}$ aryl, $C_6$-$C_{24}$ arylcarboxylate, and halide, which may, in turn, with the exception of halide, be further substituted with one or more groups selected from halide, $C_1$-$C_6$ alkyl, $C_1$-$C_{20}$ alkylcarboxylate, $C_1$-$C_6$ alkoxy, and phenyl. In some embodiments, $X^1$ is benzoate, pivalate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. More specifically, $X^1$ may be is $CF_3CO_2$, $CH_3CO_2$, $CH_3CH_2CO_2$, $CFH_2CO_2$, $(CH_3)_3CO_2$, $(CH_3)_2CHCO_2$, $(CF_3)_2(CH_3)CO_2$, $(CF_3)(CH_3)_2CO_2$, benzoate, naphthylate, tosylate, mesylate, or trifluoromethane-sulfonate. In one more preferred embodiment, $X^1$ is nitrate ($NO_3^-$).

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In certain catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, and phenyl. Most preferably, $R^2$ is phenyl or vinyl substituted with one or more moieties selected from methyl, ethyl, chloro, bromo, iodo, fluoro, nitro, dimethylamino, methyl, methoxy, and phenyl. More specifically, $R^2$ may be phenyl or —C═C$(CH_3)_2$.

Any two or more (typically two, three, or four) of $X^1$, Q*, $L^1$, $L^2$, $L^3$, $R^1$, and $R^2$ can be taken together to form a cyclic group, including bidentate or multidentate ligands, as disclosed, for example, in U.S. Pat. No. 5,312,940 to Grubbs et al. When any of $X^1$, Q*, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked.

In addition, any two or more of $X^1$, Q*, $L^1$, $L^2$, $L^3$, $R^1$, $R^2$, $R^3$, $R^{3A}$, $R^4$, and $R^{4A}$ can be taken together to form a cyclic group.

Preferably, $R^{3A}$ and $R^{4A}$ are linked to form a cyclic group so that the carbene ligand has the structure of formula (V)

(V)

wherein $R^3$ and $R^4$ are defined above, with preferably $R^3$ being alicyclic and $R^4$ being aromatic.

Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

When M is ruthenium, the complexes have the structure of formula (VI)

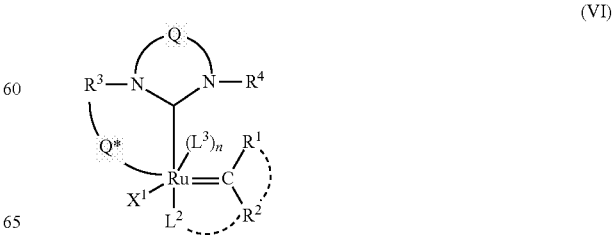

(VI)

In more particular embodiments, Q is a two-atom linkage having the structure —CR$^{11}$R$^{12}$—CR$^{13}$R$^{14}$— or —CR$^{11}$=CR$^{13}$—, preferably —CR$^{11}$R$^{12}$—CR$^{13}$R$^{14}$—, wherein R$^{11}$, R$^{12}$, R$^{13}$, and R$^{14}$ are independently selected from hydrogen, hydrocarbyl, substituted hydrocarbyl, heteroatom-containing hydrocarbyl, substituted heteroatom-containing hydrocarbyl, and functional groups. Examples of suitable functional groups include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. R$^{11}$, R$^{12}$R$^{13}$, and R$^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of R$^{11}$, R$^{12}$, R$^{13}$, and R$^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of R$^{11}$, R$^{12}$, R$^{13}$, and R$^{14}$ comprises one or more of the linkers.

In more particular aspects, R$^3$ and R$^4$ may be alkyl or aryl, and may be independently selected from alkyl, aryl, cycloalkyl, heteroalkyl, alkenyl, alkynyl, and halo or halogen-containing groups. More specifically, R$^3$ and R$^4$ may be independently selected from $C_1$-$C_{20}$ alkyl, $C_5$-$C_{14}$ cycloalkyl, $C_1$-$C_{20}$ heteroalkyl, or halide. Suitable alkyl groups include, without limitation, methyl, ethyl, n-propyl, isopropyl, isopropyl, n-butyl, isobutyl, t-butyl, octyl, decyl, and the like; suitable cycloalkyl groups include cyclopentyl, cyclohexyl, adamantyl, pinenyl, terpenes and terpenoid derivatives and the like; suitable alkenyl groups include ethenyl, n-propenyl, isopropenyl, n-butenyl, isobutenyl, octenyl, decenyl, tetradecenyl, hexadecenyl, eicosenyl, tetracosenyl, and the like; suitable alkynyl groups include ethynyl, n-propynyl, and the like.

When R$^3$ and R$^4$ are aromatic, each can be independently composed of one or two aromatic rings, which may or may not be substituted, e.g., R$^3$ and R$^4$ may be phenyl, substituted phenyl, biphenyl, substituted biphenyl, or the like. In a particular embodiment, R$^3$ and R$^4$ are independently an unsubstituted phenyl or phenyl substituted with up to three substituents selected from $C_1$-$C_{20}$ alkyl, $C_1$-$C_{20}$ alkylcarboxylate, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen $C_1$-$C_{12}$ alkyl, $C_1$-$C_{12}$ alkoxy, $C_5$-$C_{14}$ aryl, substituted, $C_5$-$C_{14}$ aryl, or halide. More particularly, R$^3$ and R$^4$ may be independently substituted with hydrogen, $C_1$-$C_4$ alkyl, $C_1$-$C_4$ alkylcarboxylate, $C_1$-$C_4$ alkoxy, $C_5$-$C_{14}$ aryl, substituted $C_5$-$C_{14}$ aryl, or halide. As an example, R$^3$ and R$^4$ are selected from cyclopentyl, cyclohexyl, adamantyl, norbonenyl, pinenyl, terpenes and terpenoid derivatives, mesityl, diisopropylphenyl or, more generally, cycloalkyl substituted with one, two or three $C_1$-$C_4$ alkyl or $C_1$-$C_4$ alkoxy groups, or a combination thereof.

In another group of catalysts having the structure of formula (II), M, m, n, X$^1$, Q*, R$^1$, and R$^2$ are as defined for the first group of catalysts, L$^1$ is a strongly coordinating neutral electron donor ligand such as any of those described for the first and second group of catalysts, and L$^2$ and L$^3$ are weakly coordinating neutral electron donor ligands in the form of optionally substituted heterocyclic groups. Again, n is zero or 1, such that L$^3$ may or may not be present. Generally, in the third group of catalysts, L$^2$ and L$^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For this group of catalysts, examples of L$^2$ and L$^3$ include, without limitation, heterocycles containing nitrogen, sulfur, oxygen, or a mixture thereof.

Complexes wherein Y is coordinated to the metal are examples of another group of catalysts, and are commonly called "Grubbs-Hoveyda" catalysts. Grubbs-Hoveyda metathesis-active metal carbene complexes may be described by the formula VIII.

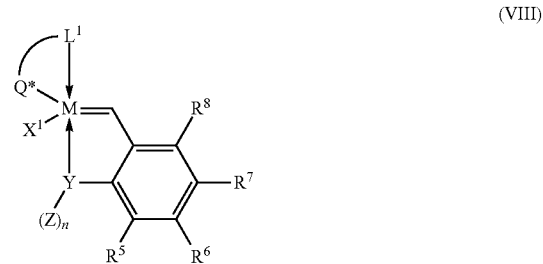

(VIII)

wherein,

M is a Group 8 transition metal, particularly Ru or Os, or, more particularly, Ru;

X$^1$ and L$^1$ are as previously defined herein;

Q* is a 2-electron anionic donor bridging moiety between L$^1$ and M forming a carbon-metal bond between L$^1$ and M;

Y is a heteroatom selected from N, O, S, and P; preferably Y is O or N;

R$^5$, R$^6$, R$^7$, and R$^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of R$^5$, R$^6$, R$^7$, and R$^8$ can be linked to form one or more cyclic groups; n is 1 or 2, such that n is 1, for the divalent heteroatoms O or S, and n is 2 for the trivalent heteroatoms N or P;

Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of X$^1$, Q*, R$^5$, R$^6$, R$^7$, and R$^8$ are linked to a support. In general, Grubbs-Hoveyda complexes useful in the invention contain a chelating alkylidene moiety of the formula IX.

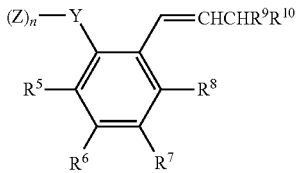

wherein Y, n, Z, $R^5$, $R^6$, $R^7$, and $R^8$ are as previously defined herein;

$R^9$ and $R^{10}$ are each, independently, selected from hydrogen or a substitutent group, selected from alkyl, aryl, alkoxy, aryloxy, $C_2$-$C_{20}$ alkoxycarbonyl, or $C_1$-$C_{20}$ trialkylsilyl, wherein each of the substituent groups is substituted or unsubstituted.

Complexes comprising Grubbs-Hoveyda ligands suitable in the invention wherein, $L^1$, $X^1$, $X^2$, and M are as described for any of the other groups of catalysts. Suitable chelating carbenes and carbene precursors are further described by Pederson et al. (U.S. Pat. Nos. 7,026,495; 6,620,955) and Hoveyda et al. (U.S. Pat. No. 6,921,735; WO0214376).

In addition to the catalysts that have the structure of formula (II), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (VIII) in which Q* is a 2-electon anionic donor bridging moiety that forms a carbon-metal bond with M;

neutral ruthenium or osmium metal carbene complexes containing metal centers that are formally in the +2 oxidation state, have an electron count of 18, are hexa-coordinated, and are of the general formula (IX) in which Q* is a 2-electon anionic donor bridging moiety that forms a carbon-metal bond with M;

cationic ruthenium or osmium metal carbene complexes containing metal centers that are formally in the +2 oxidation state, have an electron count of 16, are penta-coordinated, and are of the general formula (X) in which Q* is a 2-electon anionic donor bridging moiety that forms a carbon-metal bond with M;

cationic ruthenium or osmium metal carbene complexes containing metal centers that are formally in the +2 oxidation state, have an electron count of 18, are tetra-coordinated, and are of the general formula (XI) in which $L^2$ is a 6-electron neutral arene donor and Q* is a 2-electon anionic donor bridging moiety that forms a carbon-metal bond with M; and cationic ruthenium or osmium metal carbene complexes containing metal centers that are formally in the +2 oxidation state, have an electron count of 14, are tetra-coordinated and are of the general formula (XII) in which Q* is a 2-electon anionic donor bridging moiety that forms a carbon-metal bond with M and the alkylidene moiety possesses a formal positive charge.

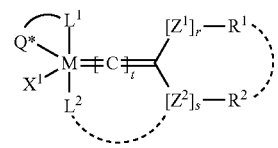

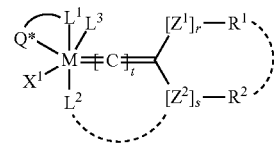

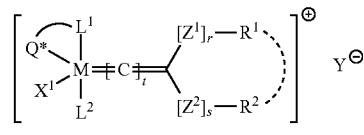

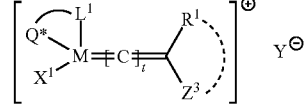

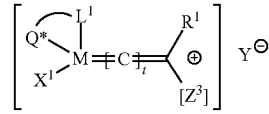

wherein: $X^1$, Q*, $L^1$, $L^2$, n, $L^3$, $R^1$, and $R^2$ are as defined for any of the previously defined four groups of catalysts; r and s are independently zero or 1; t is an integer in the range of zero to 5; Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P($OR^2$)—, —P(=O)($OR^2$)—, —C(C=O)—, —C(C=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, Q*, $L^1$, $L^2$, n, $L^3$, $Z^1$, $Z^2$, $Z^3$, $R^1$, and $R^2$ may be attached to a support via linker moieties.

As noted above, the catalyst compounds according to the invention may be prepared using the general procedures of Scheme 2 and 3 previously described. In one embodiment, for example, a C—H activated olefin metathesis catalyst compound may be prepared by contacting a carboxylate compound of the formula $M^1X^2$, wherein $M^1$ is selected from silver, lithium, sodium, potassium, rubidium, cesium, magnesium, calcium, strontium, barium, iron, zinc, or thalium, and $X^2$ is a carboxylate anion, with an olefin metathesis catalyst of the formula $(X^1)_2(L^3)_n(L^2)_kL^1$M=(C)$_m$CR$^1$R$^2$, in which, as described previously, $X^1$ is any anionic ligand, $L^1$, $L^2$, and $L^3$ are, independently, any neutral electron donor ligand, n and k are, independently, 0 or 1, m is 0, 1, or 2, M is a Group 8 transition metal, and $R^1$ and $R^2$ are the alkylidene substituents. Such C—H activation reactions may be conducted under conditions effective to promote the exchange of $X^2$ anions for the $X^1$ anionic ligands, such that a C—H activated olefin metathesis catalyst compound is produced in which M and $L^1$ are linked together by a 2-electron anionic bridging moiety Q* in a M-Q*-$L^1$ chelating ligand ring structure having a ring size of 5, 6, or 7 atoms, and the catalyst compound contains an $X^2$ anionic ligand. Typically, M is directly bonded to a carbon atom of Q* in the M-Q*-L¹ chelating ligand ring structure.

In certain embodiments, $M^1$ is silver or sodium, and the carboxylate may be of the formula $(R)_3COOM^1$, wherein R is independently selected from hydrogen, $C_1$-$C_{12}$ alkyl, substituted $C_1$-$C_{12}$ alkyl, $C_3$-$C_{12}$ cycloalkyl, substituted $C_3$-$C_{12}$ cycloalkyl, aryl or substituted aryl, wherein at least one R is not hydrogen. The R groups may be more particularly independently selected from hydrogen, $C_1$-$C_{12}$ alkyl or aryl, such as, e.g., where the $(R)_3$ groups together form t-butyl, $PhMe_2C$, $Ph_2MeC$, or $Ph_3C$.

The method of making such C—H activated catalyst compounds may further comprise additional steps, such as anionic ligand exchange reactions. For example, the C—H activated olefin metathesis catalyst compound may be contacted with an anionic ligand exchange compound of the formula $M^2X^3$, wherein $M^2$ is a cation and $X^3$ is an anion; under conditions effective to promote the exchange of $X^3$ anions for the $X^2$ anionic ligands, such that the C—H activated olefin metathesis catalyst compound contains a M-Q*-L¹ chelating ligand ring structure having a ring size of 5, 6, or 7 atoms and an $X^3$ anionic ligand.

While $M^2$ and $X^3$ are not necessarily limited, typically $M^2$ may be selected from hydrogen, ammonium, silver, lithium, sodium, potassium, rubidium, cesium, magnesium, calcium, strontium, barium, iron, zinc, or thalium, and $X^3$ may be selected from halogen, alkyl, aryl, carboxylate, alkoxy, aryloxy, sulfonate, phosphate, or nitrate.

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

Experimental

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

The following examples are to be considered as not being limiting of the invention as described herein, and are instead provided as representative examples of the catalyst compounds of the invention, the methods that may be used in their preparation, and the methods of using the inventive catalysts.

General Information—Materials and Methods

Atmosphere All reactions were carried out in dry glassware under an argon atmosphere using standard Schlenk techniques or in a Vacuum Atmospheres Glovebox under a nitrogen atmosphere unless otherwise specified.

Solvents All solvents were purified by passage through solvent purification columns and further degassed with argon as previously described (Pangborn, A. B.; Giardello, M. A.; Grubbs, R. H.; Rosen, R. K.; Timmers, F. J. *Organometallics* 1996, 15, 1518). NMR solvents for air-sensitive compounds were dried over $CaH_2$ and vacuum transferred or distilled into a dry Schlenk flask and subsequently degassed with argon.

Materials Commercially available reagents were used as received unless otherwise noted. Substrates for olefin metathesis reactions were degassed with argon and passed through a plug of neutral alumina (Brockmann I) prior to use.

Instrumentation Standard NMR spectroscopy experiments were conducted on a Varian Inova 400 MHz spectrometer, while kinetic experiments were conducted on a Varian 500 MHz spectrometer equipped with an AutoX probe. Experiments and pulse sequences from Varian's Chempack 4 software were used. Chemical shifts are reported in ppm downfield from $Me_4Si$ by using the residual solvent peak as an internal standard. Spectra were analyzed and processed using MestReNova Ver. 7. Gas chromatography data was obtained using an Agilent 6850 FID gas chromatograph equipped with a DB-Wax Polyethylene Glycol capillary column (J&W Scientific). High-resolution mass spectrometry (HRMS) data was obtained on a JEOL MSRoute mass spectrometer using FAB+ ionization, except where specified.

EXAMPLES

Example 1

Preparation of C—H Activated Catalyst Complexes from Ru-complex 4

By reaction of $(H_2IMes)RuCl_2[=CH-o-(O^iPr)C_6H_4]$ (4) and two equivalent of RCOOAg (R=$^t$Bu, $PhMe_2C$) at room temperature, metallacycle complexes $\{[2-(CH_2)-4,6-Me_2(C_6H_2)](C_3N_2H_4)-(Mes)\}Ru(OCOR)[=CH-o-(O^iPr)C_6H_4]$ (R=$^t$Bu(7a), $PhMe_2C$ (7b)) were obtained as an air-stable dark green solids in good yields (Scheme 4). In this reaction, disubstituted complex (8) was also observed at early reaction time. Then, C—H bond activation of methyl group of mesityl group in the NHC ligand and formation of corresponding carboxylic acid afforded 7. The molecular structures of 7a and 7b were confirmed by X-ray crystallography. As shown in FIGS. 4 and 5, both 7a and 7b have 6-membered chelates consisting of ruthenium and the NHC ligand.

Scheme 4

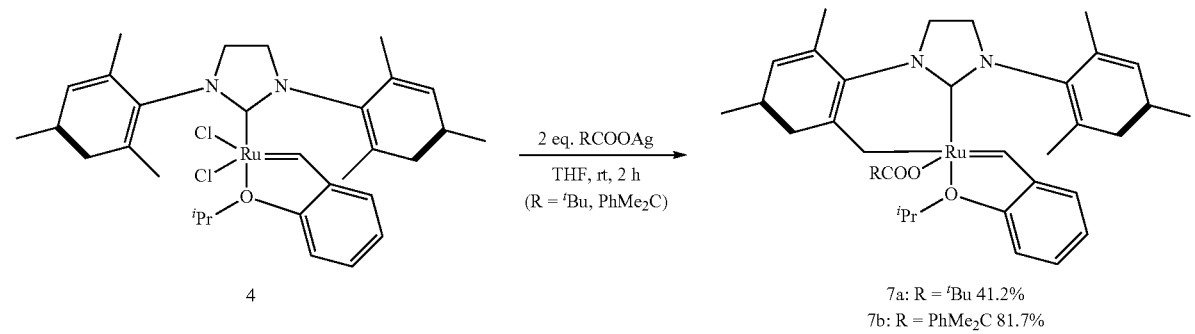

7a: R = $^t$Bu 41.2%
7b: R = $PhMe_2C$ 81.7%

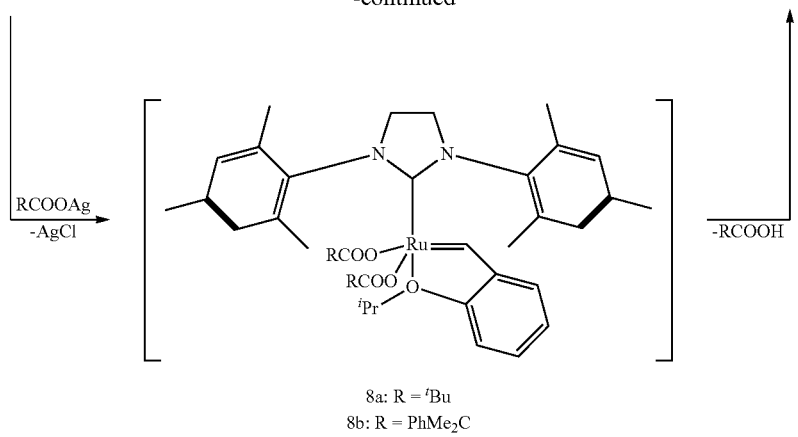

8a: R = tBu
8b: R = PhMe₂C

Representative characterization data for complex 7a is as follows:

¹H NMR (500 MHz, C₆D₆): δ/ppm 15.91 (s, 1H), 7.15-7.11 (m, 2H), 7.06 (s, 1H), 6.95 (s, 1H), 6.92 (s, 1H), 6.73-6.70 (m, 1H), 6.63 (s, 1H), 6.49 (d, J=8.5 Hz, 1H), 4.68 (sep, J=6.4 Hz, 1H), 3.87-3.83 (m, 1H), 3.45-3.38 (m, 2H), 3.29 (d, J=9.8 Hz, 1H), 3.21-3.15 (m, 1H), 2.46 (s, 3H), 2.36 (s, 3H), 2.26 (s, 3H), 2.21 (s, 3H), 2.17 (d, J=9.8 Hz, 1H), 2.12 (s, 3H), 1.48 (d, J=6.4 Hz, 3H), 1.26 (s, 9H), 1.16 (d, J=6.4 Hz, 3H). ¹³C NMR (125.7 MHz, C₆D₆): δ/ppm 280.8, 223.6, 186.6, 154.6, 144.7, 142.7, 142.3, 139.7, 138.4, 137.7, 136.8, 134.5, 130.9, 130.7, 128.8, 128.1, 128.0, 126.9, 123.6, 123.1, 112.7, 54.1, 50.3, 39.5, 28.5, 22.2, 21.7, 21.4, 21.3, 19.9, 18.7, 18.6, 17.9. HRMS (FAB+): Calculated: 656.2552, Found: 656.2548.

Example 2

Preparation of C—H Activated Catalyst Complexes from Ru-complex 9

In the same manner as Scheme 4, (H₂IMes)Ru(OTf)₂[=CH-o-(OⁱPr)C₆H₄] (9) (prepared as described in Krause, J. O.; Nuyken, O.; Wurst, K.; Buchmeiser, M. R. *Chem. Eur. J.* 2004, 10, 777) gave chelate complexes {[2-(CH₂)-4,6-Me₂(C₆H₂)](C₃N₂H₄)(Mes)}Ru(OCOR)[=CH-o-(OⁱPr)C₆H₄](R=tBu (7a), Ph₂MeC (7c), Ph₃C (7d)) in reactions with corresponding sodium salts (Scheme 5). The products were all air-stable in solid state. In these reactions, formation of disubstituted complexes (8) at early stage of reaction and subsequent formation of carboxylic acid were also observed.

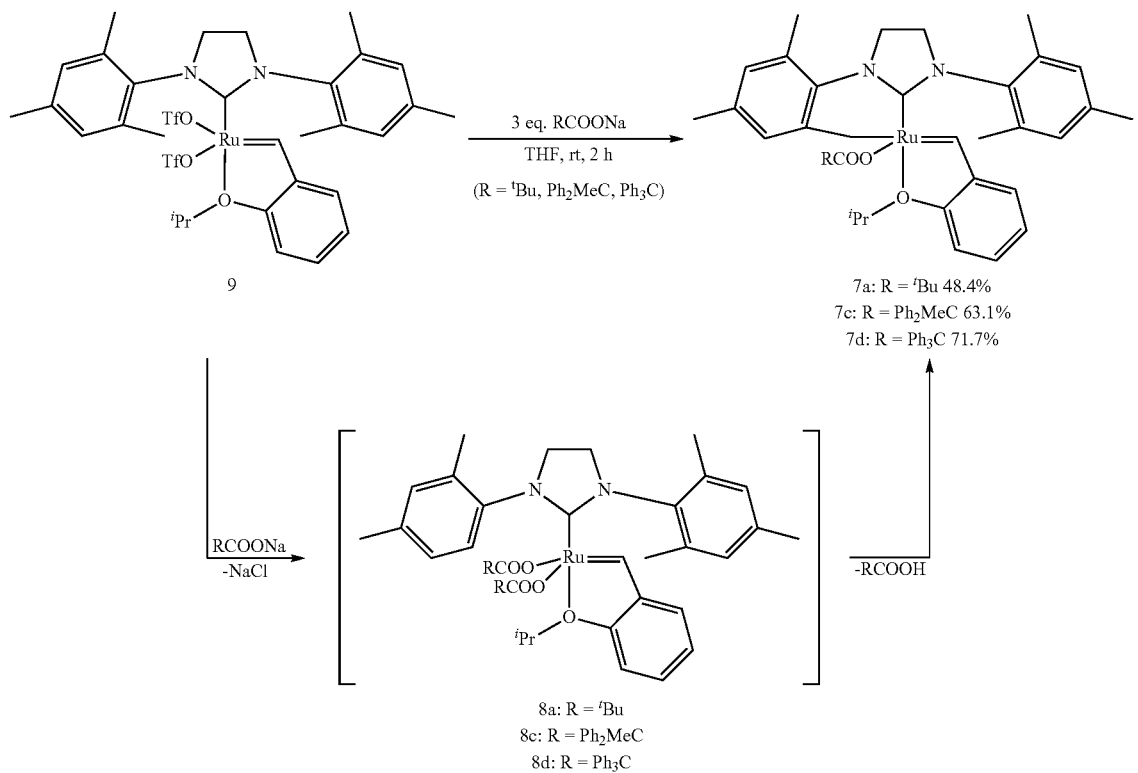

7a: R = tBu 48.4%
7c: R = Ph₂MeC 63.1%
7d: R = Ph₃C 71.7%

8a: R = tBu
8c: R = Ph₂MeC
8d: R = Ph₃C

Example 3
Preparation of C—H Activated Catalyst Complexes from Ru-complex 10

By reaction of (H$_2$IMesDipp)RuCl$_2$[=CH-o-(O$^i$Pr)C$_6$H$_4$] (10), which had an asymmetric NHC ligand containing one 2,6-diisopropylphenyl group instead of mesityl group in 4, and silver pivalate, {[2-(CH$_2$)-4,6-Me$_2$(C$_6$H$_2$)](C$_3$N$_2$H$_4$)(Dipp)}Ru(CO$^t$Bu)[=CH-o-(O$^i$Pr)C$_6$H$_4$] (11) was obtained as an air-stable dark green solid in good yield (Scheme 6). During the reaction, disubstituted complex (12) was formed and none of the complexes resulting from C—H bond activation in the 2,6-diisopropylphenyl group were observed. The crystal structure of 11 determined by X-ray crystallography (FIG. 6) showed a 6-membered chelate and clearly indicated that C—H bond activation had occurred at the methyl group of the mesityl group in the NHC ligand.

Scheme 6

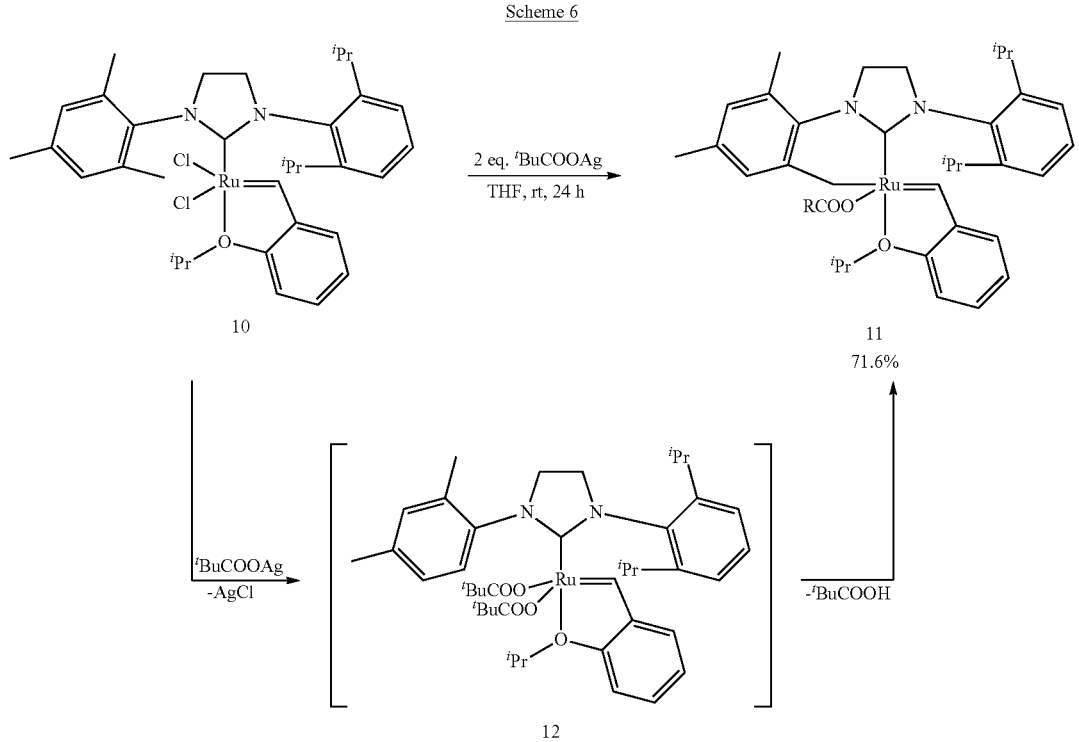

Example 4
Syntheses of RuCl$_2$ Complexes Comprising an Asymmetric NHC Ligand that Contains an Adamantyl Group Asymmetric NHC salts 17a-f containing an adamantyl group were synthesized by modifying a reported procedure (Paczal, A.; Benyei, A. C.; Kotschy, A. *J. Org. Chem.* 2006, 71, 5069) as outlined in Scheme 7. All products were obtained in good to excellent yield.

Scheme 7

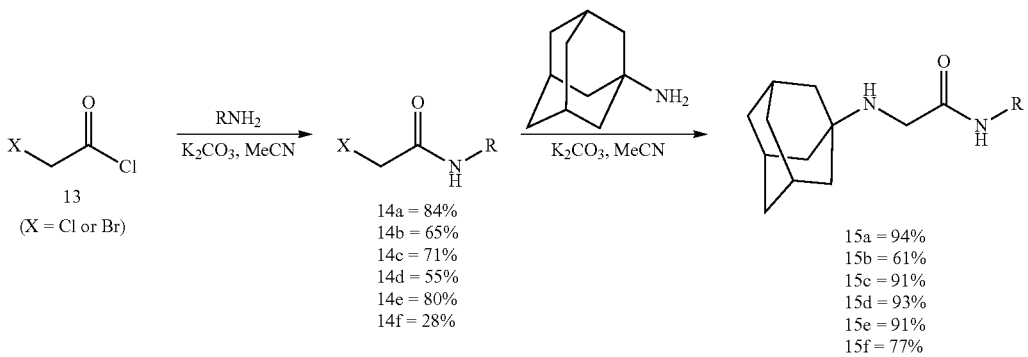

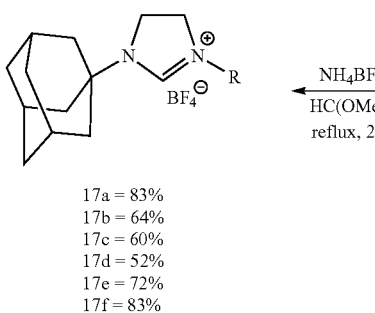

17a = 83%
17b = 64%
17c = 60%
17d = 52%
17e = 72%
17f = 83%

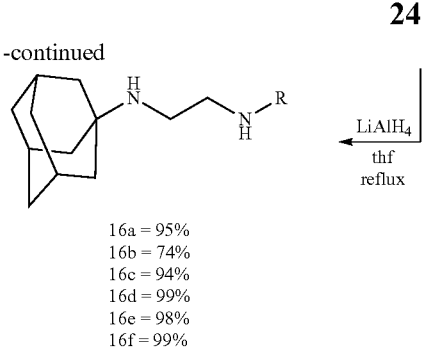

16a = 95%
16b = 74%
16c = 94%
16d = 99%
16e = 98%
16f = 99%

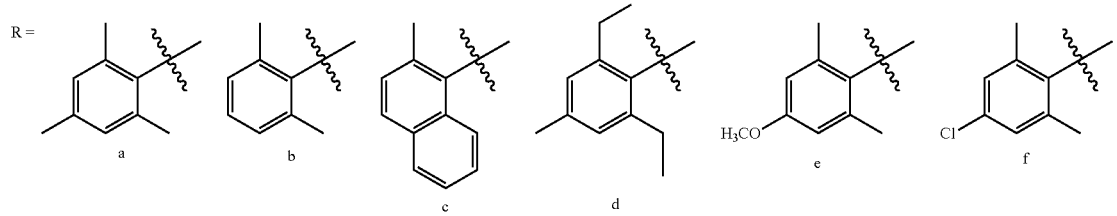

Dichloro ruthenium alkylidene catalysts (18a-f) having the NHC's 17a-f were also synthesized by modifying a reported procedure (Jafarpour, L.; Hillier, A. C.; Nolan, S. P. *Organometallics* 2002, 21, 442) as outlined in Scheme 8. They were obtained as air-stable green solids in excellent yield. Structures of 18a-c were determined by X-ray crystallography and are shown in FIGS. 7-9.

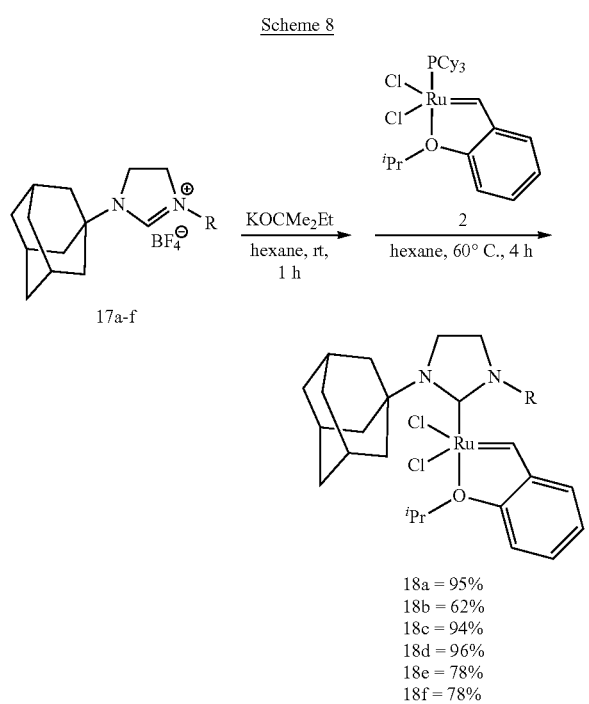

18a = 95%
18b = 62%
18c = 94%
18d = 96%
18e = 78%
18f = 78%

Representative characterization data for complex 18a is as follows:

$^1$H NMR (500 MHz, C$_6$D$_6$): δ/ppm 17.13 (s, 1H), 7.21-7.13 (m, 2H), 6.85 (s, 2H), 6.75-6.73 (m, 1H), 6.46 (d, J=8.2 Hz, 1H), 4.58 (scp, J=6.1 Hz, 1H), 3.30-3.28 (m, 4H), 2.95 (br s, 6H), 2.35 (s, 6H), 2.31 (br s, 3H), 2.24 (s, 3H), 1.90 (br d, 3H), 1.69 (br d, 3H), 1.58 (d, J=6.1 Hz, 6H). $^{13}$C NMR (125.7 MHz, C$_6$D$_6$): δ/ppm 307.9, 210.4, 153.1, 146.8, 140.7, 138.8, 138.6, 130.3, 130.2, 123.7, 122.8, 113.9, 74.6, 57.5, 51.4, 44.7, 42.6, 36.7, 30.8, 22.8, 21.5, 18.9. HRMS (FAB+): Calculated: 642.1718, Found: 642.1742.

Example 5

Preparation of C—H Activated Catalyst Complexes from Ru-complexes 18a-c

A reaction of (H$_2$IAdmMes)RuCl$_2$[═CH-o-(O$^i$Pr)C$_6$H$_4$] (18a) and silver pivalate gave [(C$_{10}$H$_{14}$)(C$_3$N$_2$H$_4$)(Mes)]Ru (OCO$^t$Bu)[═CH-o-(O$^i$Pr)C$_6$H$_4$] (19a) resulting from C—H bond activation at the adamantyl group as an air-stable red-purple solid (Scheme 9). 19a was easily prepared, after a short reaction time and was purified by simply washing and extraction with common organic solvents. Unlike the case of 4 or 10, products derived from C—H bond activation at mesityl group were not observed. In the reactions with silver pivalate, {H$_2$IAdm[2,6-(CH$_3$)$_2$C$_6$H$_3$]}RuCl$_2$[═CH-o-(O$^i$Pr)C$_6$H$_4$] (18b) and {H$_2$IAdm[2-(CH$_3$)C$_{10}$H$_6$]}RuCl$_2$[═CH-o-(O$^i$Pr)C$_6$H$_4$] (18c) also afforded corresponding metallacycle catalysts {(C$_{10}$H$_{14}$)(C$_3$N$_2$H$_4$)[2,6-(CH$_3$)$_2$C$_6$H$_3$]}Ru(OCO$^t$Bu)[═CH-o-(O$^i$Pr)C$_6$H$_4$] (19b) and {(C$_{10}$H$_{14}$)(C$_3$N$_2$H$_4$)-[2-(CH$_3$)C$_{10}$H$_6$]}Ru(OCO$^t$Bu)[═CH-o-(O$^i$Pr)C$_6$H$_4$] (19c) which were generated by C—H bond activation at the adamantyl groups as shown in Scheme 9. The structure of 19a having a 5-membered chelate was determined by X-ray crystallography (FIG. 10).

Scheme 9

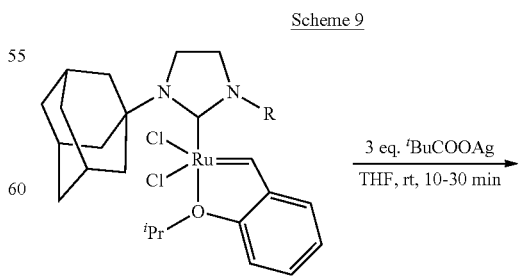

18a: R = 2,4,6-(CH$_3$)$_3$C$_6$H$_2$
18b: R = 2,6-(CH$_3$)$_2$C$_6$H$_3$
18c: R = 2-(CH$_3$)C$_{10}$H$_6$

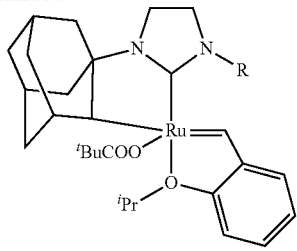

19a: R = 2,4,6-(CH$_3$)$_3$C$_6$H$_2$ 59.3%
19b: R = 2,6-(CH$_3$)$_2$C$_6$H$_3$ 37.5%
19c: R = 2-(CH$_3$)C$_{10}$H$_6$ 52.3%

R = mesityl, 2,6-dimethylphenyl, 2-methylnaphthalen-1-yl)

Representative characterization data for complex 19a is as follows:

$^1$H NMR (500 MHz, C$_6$D$_6$): δ/ppm 14.87 (s, 1H), 7.47 (dd, J=7.3 Hz, J=1.2 Hz, 1H), 7.27-7.24 (m, 1H), 6.90 (t, J=7.3 Hz, 1H), 6.82 (s, 1H), 6.74 (s, 1H), 6.71 (d, J=8.2 Hz, 1H), 4.80 (sep, J=6.4 Hz, 1H), 4.19 (s, 1H), 3.46-3.36 (m, 2H), 3.29-3.14 (m, 2H), 2.53 (br s, 1H), 2.43 (s, 3H), 2.27 (s, 3H), 2.20 (s, 3H), 2.11-2.08 (br m, 2H), 2.03-2.01 (br m, 1H), 1.95-1.92 (br m, 1H), 1.85-1.81 (br m, 1H), 1.65-1.64 (br m, 1H), 1.56-1.47 (br m, 2H), 1.52 (d, J=6.4 Hz, 3H), 1.40-1.36 (br m, 1H), 1.25 (s, 9H), 1.21-1.19 (br m, 1H), 1.17 (d, J=6.4 Hz, 3H), 1.06-1.02 (br m, 1H), 0.68-0.65 (br m, 1H). $^{13}$C NMR (125.7 MHz, C$_6$D$_6$): δ/ppm 258.9, 216.0, 154.6, 144.2, 138.3, 137.4, 137.1, 136.7, 130.2, 130.0, 125.8, 123.5, 123.5, 114.2, 74.7, 68.9, 63.0, 52.0, 43.7, 41.6, 40.9, 39.9, 38.6, 38.4, 37.2, 34.1, 31.4, 30.3, 28.8, 27.9, 21.9, 21.5, 21.4, 19.5, 19.3. HRMS (FAB+): Calculated: 672.2866, Found: 672.2851.

Example 6

Exchange of the Pivalate Ligand in Complex 19a with Other X-type Ligands

The pivalyl ligand of 19a was easily replaced by other anionic ligands. As shown in Scheme 10, when 19a was reacted with hydrogen chloride or sodium iodide, a chloro catalyst [(C$_{10}$H$_{14}$)(C$_3$N$_2$H$_4$)-(Mes)]RuCl[=CH-o-(O$^i$Pr)C$_6$H$_4$] (20a) or an iodo catalyst [(C$_{10}$H$_{14}$)(C$_3$N$_2$H$_4$)(Mes)]RuI[=CH-o-(O$^i$Pr)—C$_6$H$_4$] (20b) were afforded, respectively. Also potassium 2,6-diisopropylphenoxide or potassium pentachlorophenoxide reacted with 19a and afforded phenoxy substituted catalysts [(C$_{10}$H$_{14}$)(C$_3$N$_2$H$_4$)-(Mes)]Ru[O(2,6-$^i$Pr$_2$C$_6$H$_3$)][=CH-o-(O$^i$Pr)C$_6$H$_4$] (21a) or [(C$_{10}$H$_{14}$)(C$_3$N$_2$H$_4$)(Mes)]Ru[O(C$_6$Cl$_5$)][=CH-o-(O$^i$Pr)C$_6$H$_4$] (21b), respectively as displayed in Scheme 11. 20 and 21 were all air-stable and easy to handle. Complexes 20b, 21a and 21b were purified by simple wash and extraction instead of silica gel chromatography and were obtained in excellent yield. The structure of 21a was confirmed by X-ray crystallography (FIG. 11).

Scheme 10

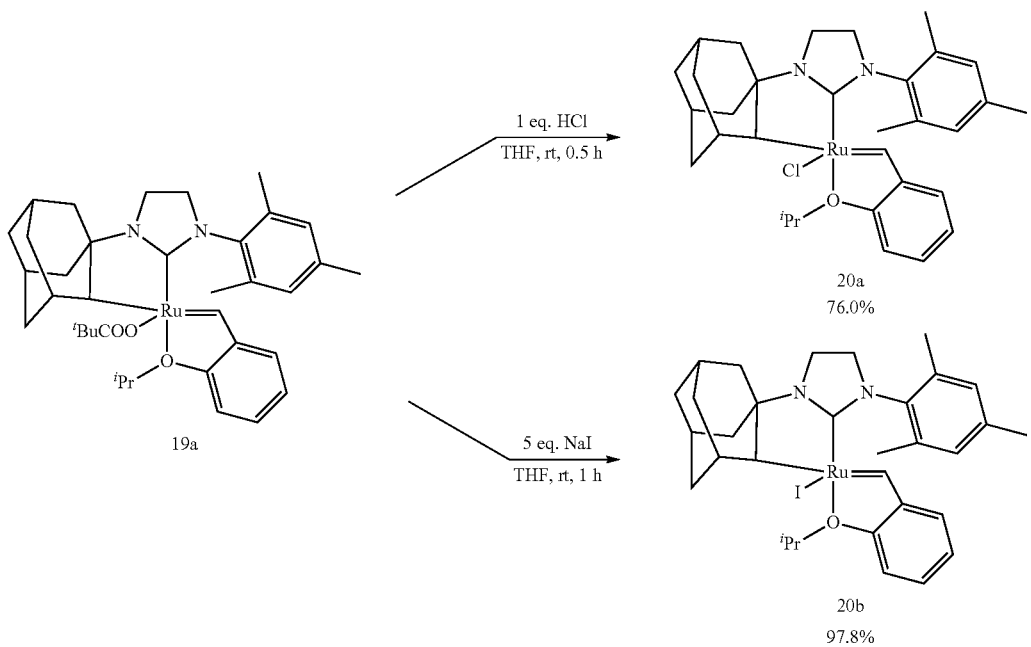

Representative characterization data for complex 20b is as follows:

$^1$H NMR (400 MHz, C$_6$D$_6$) δ 13.42 (s, 1H), 7.38 (dd, J=8, 4 Hz, 1H), 7.15 (m, 1H), 6.97 (br s, 1H), 6.80 (dt, J=8, 1 Hz, 1H), 6.76 (br s, 1H), 6.64 (d, J=8 Hz, 1H), 4.81 (sept, J=4 Hz, 1H), 3.46 (q, J=8 Hz, 1H), 3.37-3.30 (m, 1H), 3.11-3.06 (m, 2H), 2.61 (br s, 1H), 2.56 (s, 3H), 2.41 (s, 3H), 2.40 (br s, 1H), 2.13 (s, 3H), 2.03 (br s, 1H), 1.91 (d, J=4 Hz, 3H), 1.86-1.79 (m, 2H), 1.65 (br s, 2H), 1.62 (d, J=4 Hz, 3H), 1.59-1.57 (m, 1H), 1.43-1.37 (m, 3H), 2.30 (br d, J=8 Hz, 2H), 0.54 (br d, J=16 Hz, 1H). $^{13}$C NMR (126 MHz, C$_6$D$_6$) δ 236.56, 215.48, 154.59, 141.54, 139.13, 138.09, 137.45, 135.36, 125.96, 123.47, 122.63, 112.99, 81.52, 75.78, 63.40, 52.52, 42.24, 41.09, 39.39, 38.12, 37.54, 37.25, 33.81, 30.63, 29.64, 22.72, 21.76, 21.16, 20.99, 19.28. HRMS (FAB+): Calculated—698.1316, Found—698.1343.

Scheme 11

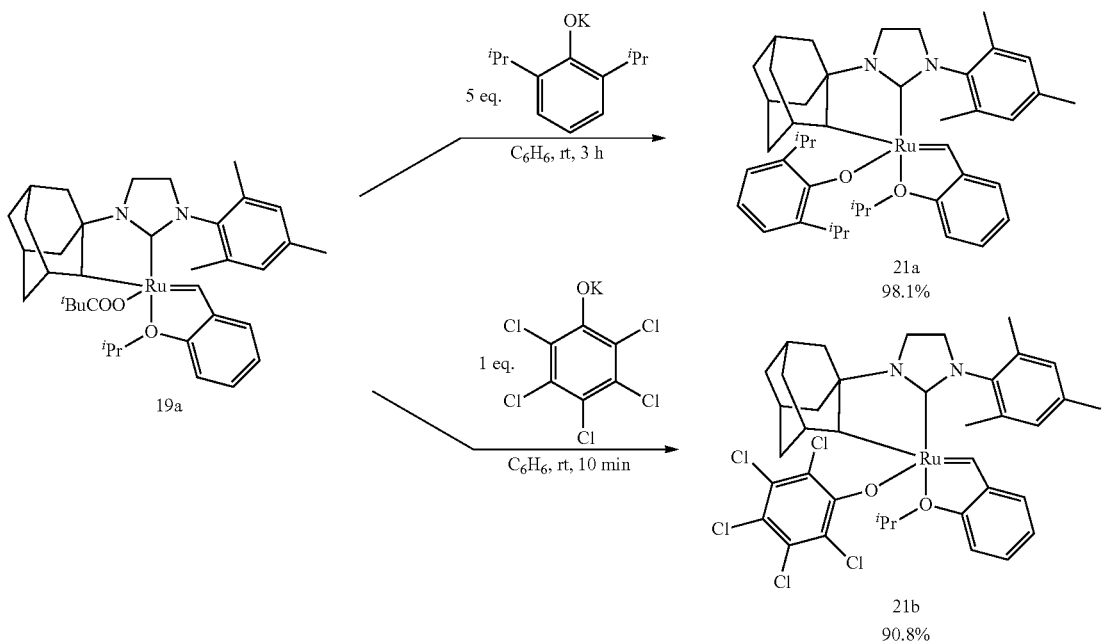

Representative characterization data for complex 21b is as follows:

$^1$H NMR (500 MHz, $C_6D_6$) δ 14.78 (s, 1H), 7.41-7.33 (m, 1H), 7.21-7.15 (m, 1H), 6.80 (t, J=7.4 Hz, 1H), 6.66 (d, J=1.7 Hz, 1H), 6.46 (d, J=8.4 Hz, 1H), 6.22 (d, J=1.6 Hz, 1H), 4.44 (sept, J=6.2 Hz, 1H), 4.40 (s, 1H), 3.28-3.14 (m, 2H), 3.14-2.98 (m, 2H), 2.32 (s, 3H), 2.20 (d, J=3.1 Hz, 1H), 2.15 (s, 3H), 2.00 (s, 4H), 1.88 (ddt, J=29.0, 11.0, 2.8 Hz, 2H), 1.77-1.62 (m, 2H), 1.57 (s, 1H), 1.50 (d, J=6.3 Hz, 3H), 1.48-1.29 (m, 3H), 1.14-0.93 (m, 2H), 0.74 (d, J=6.1 Hz, 3H), 0.55 (d, J=12.5, 1H). $^{13}$C NMR (126 MHz, $C_6D_6$) δ 254.34, 214.38, 160.36, 154.03, 144.19, 137.91, 137.60, 136.08, 135.99, 129.10, 128.95, 126.54, 123.34, 123.03, 113.70, 113.05, 74.53, 67.47, 63.08, 51.11, 42.65, 41.41, 39.76, 37.82, 37.80, 36.90, 32.90, 30.77, 29.56, 21.28, 21.09, 20.26, 18.47, 18.17.=

Example 7

Exchange of the Iodide Ligand in Complex 20b with Other X-type Ligands

When 20b was reacted with silver 2-mesitylenesulfonate, iodo ligand of 20b was replaced by sulfonate ligand and [($C_{10}H_{14}$)($C_3N_2H_4$)(Mes)]Ru(SO$_3$Mes)[=CH-o-(O$^i$Pr)$C_6H_4$] (22a) was yielded. Compounds 22b-n (Scheme 12) were synthesized in a similar manner as described for 22a. An x-ray crystal structure confirming the structure of 22e is shown in FIG. 12.

Scheme 12

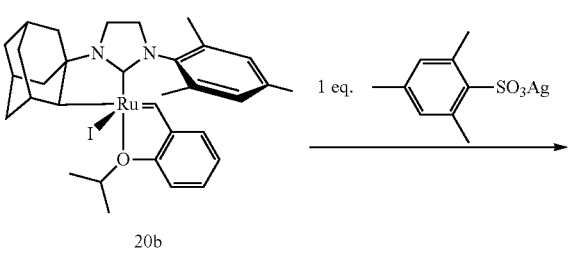

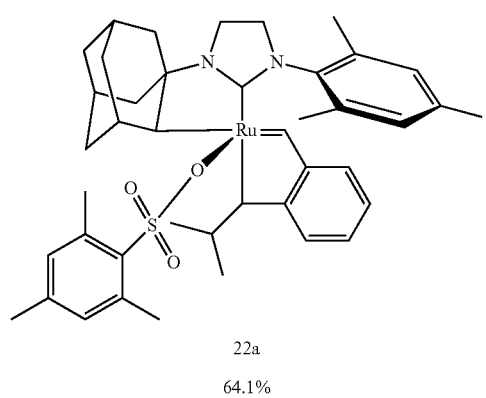

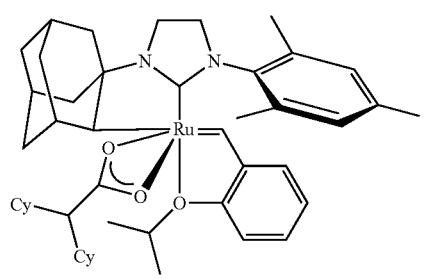 22b
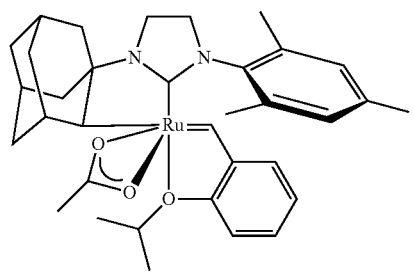 22c
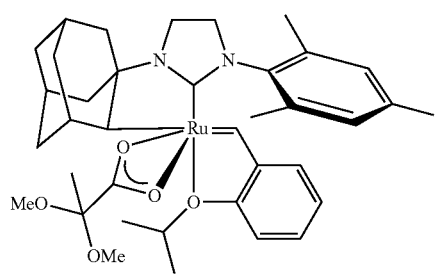 22d
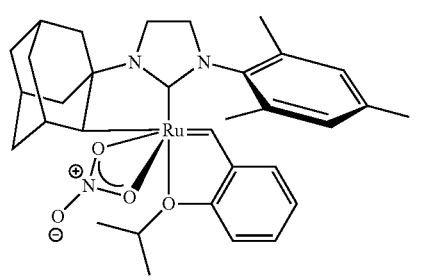 22e
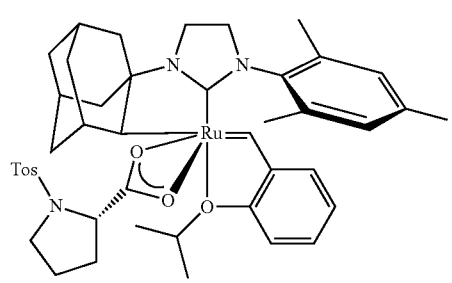 22f
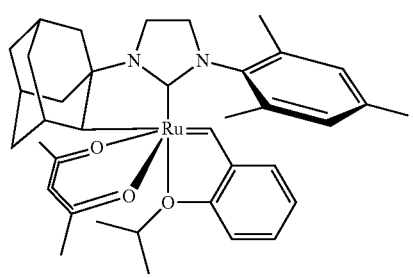 22g
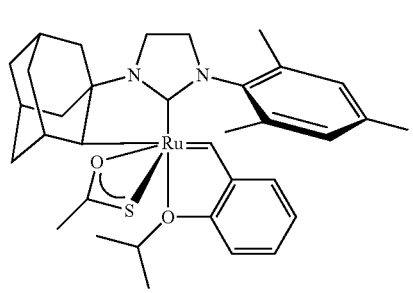 22h
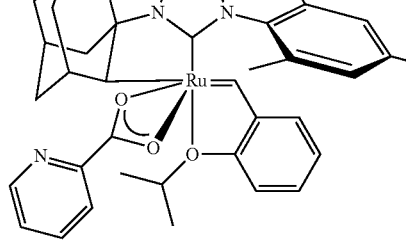 22i
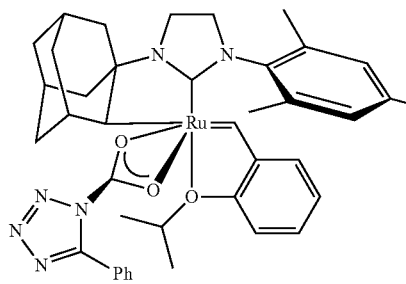 22j
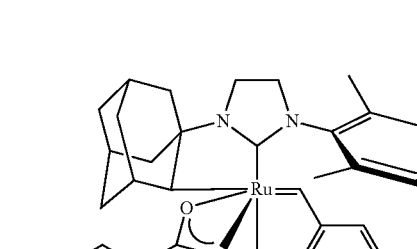 22k

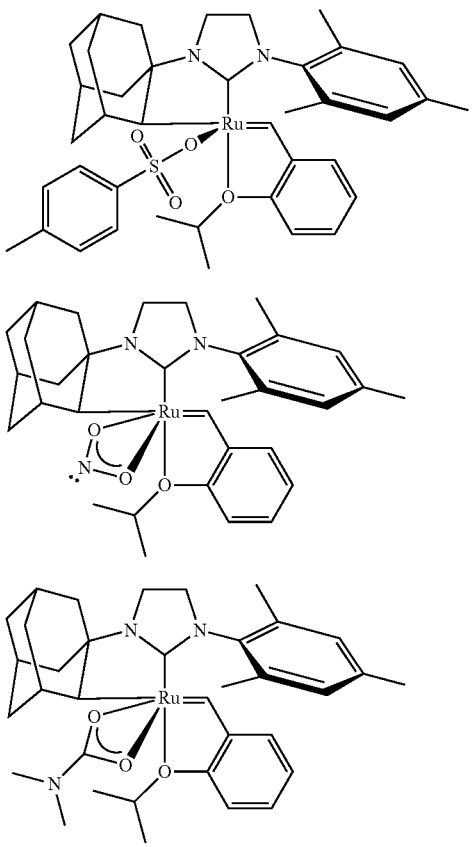

Representative characterization data for complex 22b is as follows:

¹H NMR (400 MHz, C₆D₆) δ 14.94 (s, 1H), 7.41 (dd, J=8, 4 Hz, 1H), 7.25 (dt, J=8, 4 Hz, 1H), 6.87-6.83 (m, 2H), 6.80 (br s, 1H), 6.72 (br d, J=8 Hz, 1H), 4.78 (sept, J=8 Hz, 1H), 4.08 (s, 1H), 3.45-3.13 (m, 4H), 2.47 (br s, 1H), 2.44 (s, 3I-1), 2.33 (s, 1H), 2.25 (s, 1H), 2.10-1.30 (m, 10H), 2.07 (br s, 1H), 1.98 (br d, J=8 Hz, 3H), 1.88 (br d, J=8 Hz, 4H), 1.79 (br s, 3H), 1.76 (br s, 2H), 1.64 (br s, 4H), 1.60 (d, J=4 Hz, 4H), 3.34 (br d, J=16 Hz, 3H), 1.39 (br s, 1H), 1.36 (d, J=4 Hz, 5H), 1.17 (br d, J=8 Hz, 2H), 1.07 (br d, J=8 Hz, 2H), 0.63 (br d, J=12 Hz, 1H). ¹³C NMR (101 MHz, C₆D₆) δ 258.83, 214.74, 183.61, 153.90, 143.52, 137.70, 136.58, 136.43, 136.03, 129.47, 129.20, 124.98, 122.86, 122.83, 113.34, 73.83, 67.67, 62.30, 57.15, 51.31, 42.77, 40.96, 40.04, 37.88, 37.58, 36.76, 33.30, 30.71, 29.60, 21.68, 21.35, 20.86, 18.65, 18.49. HRMS (FAB+, (M+H)—H₂): Calculated—793.3883, Found—793.3894.

Representative characterization data for complex 22c is as follows:

¹H NMR (400 MHz, C₆D₆) δ 14.95 (s, 1H), 7.47 (dd, J=7.6, 1.6 Hz, 1H), 7.25 (t, J=7.2 Hz, 1H), 6.88 (dt, J=7.6, 1.2 Hz, 1H), 6.77 (br s, 1H), 6.70 (br s, 1H), 6.65 (br d, J=8.4 Hz, 1H), 4.76 (sept, J=6.0 Hz, 1H), 4.06 (s, 1H), 3.47 (q, J=8.8 Hz, 1H), 3.38-3.21 (m, 4H), 2.43 (s, 3H), 2.40 (br s, 1H), 2.33 (s, 3H), 2.15 (br s, 4H), 2.15-1.04 (m, 2H), 1.98-1.95 (m, 1H), 1.87-1.83 (m, 1H), 1.78 (s, 3H), 1.69 (br s, 1H), 1.57 (d, J=6.4 Hz, 1H), 1.56-1.53 (m, 2H), 1.22-1.15 (m, 2H), 1.05 (d, J=6.4 Hz, 3H), 0.73 (br d, J=12 Hz, 1H).

¹³C NMR (101 MHz, C₆D₆) δ 259.69, 215.65, 180.15, 154.57, 143.79, 137.76, 137.41, 136.81, 136.42, 129.55, 129.24, 125.51; 123.20, 123.19, 112.90, 74.01, 68.79, 67.84, 62.82, 51.44, 43.38, 41.62, 40.64, 38.27, 37.97, 37.72, 33.59, 31.21, 30.03, 25.84, 24.43, 21.35, 21.04, 20.73, 18.75, 18.48. HRMS (FAB+, (M+H)—H₂): Calculated—629.2318, Found—629.2345.

Representative characterization data for complex 22d is as follows:

¹H NMR (600 MHz, C₆D₆) δ 14.88 (s, 1H), 7.43 (br d, J=12 Hz, 1H), 7.23 (t, J=6 Hz, 1H), 6.94 (br s, 1H), 6.86 (t, J=6 Hz, 1H), 6.74-6.71 (m, 2H), 4.87 (br s, 1H), 4.16 (s, 1H), 3.50-3.19 (m, 10H), 2.47 (br s, 1H), 2.45 (s, 3H), 2.40 (s, 3H), 2.20 (s, 3H), 2.13-2.08 (m, 2H), 2.01 (br d, J=12 Hz, 1H), 1.96 (br d, J=12 Hz, 1H), 1.82 (br d, J=12 Hz, 1H), 1.66 (br s, 1H), 1.63 (d, J=6 Hz, 3H), 1.57-1.54 (m, 1H), 1.50-1.48 (m, 1H), 1.43 (br d, J=12 Hz, 1H), 1.38 (s, 3H), 1.27 (br d, J=6 Hz, 3H), 1.17 (br d, J=12 Hz, 1H), 1.10-1.09 (m, 2H), 0.68 (br d, J=6 Hz, 1H). ¹³C NMR (151 MHz, C₆C₆) δ 259.06, 216.37, 177.95, 154.78, 144.04, 138.48, 137.86, 136.61, 136.38, 130.46, 129.48, 125.96, 123.52, 123.39, 113.89, 99.58, 75.37, 69.60, 63.10, 51.94, 43.58, 41.83, 40.83, 38.50, 38.32, 37.63, 33.94, 31.45, 30.30, 21.70, 21.41, 21.17, 20.99, 19.11, 18.88. HRMS (FAB+, (M+H)—H₂): Calculated—703.2685, Found—703.2682.

Representative characterization data for complex 22e is as follows:

¹H NMR (400 MHz, C₆D₆) δ 15.22 (s, 1H), 7.37 (d, J=7.2 Hz, 1H), 7.18 (t, J=7.6 Hz, 1H), 6.98 (s, 1H), 6.82 (t, J=7.6 Hz, 1H), 6.66 (s, 1H), 6.48 (d, J=8.4 Hz, 1H), 4.57 (sept, J=6.0 Hz, 1H), 4.17 (s, 1H), 3.43 (q, J=9.6 Hz, 1H), 3.28-3.15 (m, 3H), 2.38 (d, J=8.4 Hz, 6H), 2.25 (br s, 1H), 2.15-2.09 (m, 4H), 2.03-1.97 (m, 2H), 1.90-1.87 (m, 1H), 1.77 (br d, J=15.2 Hz, 1H), 1.65 (br s, 1H), 1.55-1.47 (m, 2H), 1.42 (d, J=5.2 Hz, 3H), 1.14-1.10 (m, 3H), 0.96 (d, J=6.0 Hz, 3H), 0.58 (br d, J=12 Hz, 1H). ¹³C NMR (101 MHz, C₆D₆) δ 265.80, 265.55, 214.16, 154.72, 143.60, 137.69, 137.40, 136.24, 135.45, 130.11, 129.36, 126.83, 123.38, 123.35, 113.00, 74.32, 66.78, 63.05, 51.36, 43.14, 41.84, 40.34, 37.95, 37.81, 37.65, 33.33, 30.98, 29.83, 21.25, 21.09, 20.28, 18.56, 17.44. HRMS (FAB+, M-NO₃): Calculated—571.2263, Found—571.2273.

Example 8

Investigations Employing Complex 23 as a Ru Precursor

When (H₂IMes)RuCl(OTf)[=CH-o-(OⁱPr)C₆H₄] (23) (prepared as described in Krause, J. O.; Nuyken, O.; Wurst, K.; Buchmeiser, M. R. Chem. Eur. J. 2004, 10, 777) was reacted with RCOONa (R=ᵗBu, Ph₃C), the triflate ligand of 23 was selectively substituted by carboxylate ligand and (H₂IMes)RuCl(OCOR)—[=CH-o-(OⁱPr)C₆H₄](R=ᵗBu (24a), Ph₃C (24d)) was afforded in an excellent yield (Scheme 13). In this reaction, neither substitution of the chloro ligand of 23 nor C—H bond activation at the mesityl group of 24 was observed. The molecular structure of 24d determined by X-ray crystallography is shown in FIG. 13.

Scheme 13

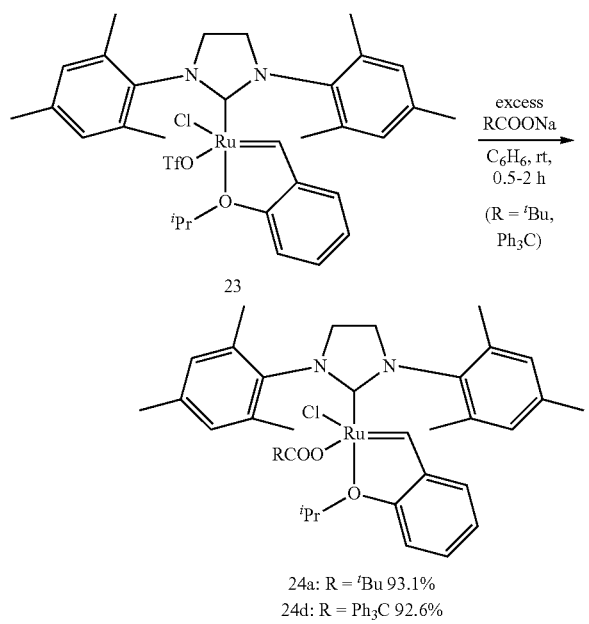

24a: R = $^t$Bu 93.1%
24d: R = Ph$_3$C 92.6%

Example 9

Comparative Results for the Cross-metathesis of Allylbenzene and Cis-1,4-Diacetoxy-2-butene with Catalysts 1-4 and 7-24

Selected data of cross metathesis reaction of allylbenzene (25) and cis-1,4-diacetoxy-2-butene (26) yielding 1-acetoxy-4-phenyl-2-butene (27) (Scheme 14) are summarized in Tables 1-3.

Scheme 14

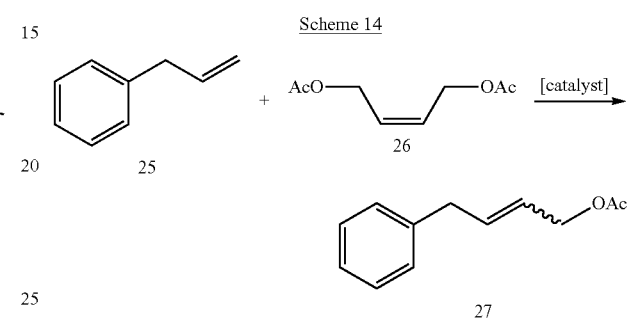

TABLE 1

Cross metathesis reactions of allylbenzene (25) and cis-1,4-diacetoxy-2-butene (26) by catalysts $\{[2-(CH_2)-4,6-Me_2(C_6H_2)](C_3N_2H_4)(Ar)\}Ru(X)[=CH—o-(O^iPr)C_6H_4]^a$

| | Catalyst | | Catalyst loading | Solvent | Temperature | Time | conversion[b] | E/Z[c] | Time | conversion[b] | E/Z[c] |
|---|---|---|---|---|---|---|---|---|---|---|---|
| Entry No. | Ar | X | mol % | — | °C. | min | % | — | min | % | — |
| 1 | 7a | Mes | $^t$BuCOO | 2.5 | C$_6$H$_6$ | 23 | 10 | 57.5 | 1.44 | 60 | 57.4 | 1.44 |
| 2 | 7b | Mes | PhMe$_2$CCOO | 2.5 | C$_6$H$_6$ | 23 | 10 | 56.6 | 1.45 | 60 | 57.6 | 1.46 |
| 3 | 7c | Mes | Ph$_2$MeCCOO | 2.5 | C$_6$H$_6$ | 23 | 10 | 62.2 | 1.82 | 60 | 64.4 | 1.88 |
| 4 | 7d | Mes | Ph$_3$CCOO | 2.5 | C$_6$H$_6$ | 23 | 10 | 50.9 | 2.16 | 60 | 61.9 | 2.41 |
| 5 | 11 | Dipp | $^t$BuCOO | 2.5 | C$_6$H$_6$ | 23 | 10 | 69.6 | 1.11 | 60 | 70.6 | 1.13 |

[a]All reactions were carried out using 0.20 mmol of allylbenzene (25), 0.40 mmol of cis-1,4-diacetoxy-2-butene (26), 0.10 mmol of tridecane (internal standard for GC analysis) and 0.005 mmol of catalyst in 1.0 ml of solvent.
[b]Conversion of allylbenzene (25) to 1-acetoxy-4-phenyl-2-butene (27) determined by GC analysis.
[c]Molar ratio of E isomer and Z isomer of 1-acetoxy-4-phenyl-2-butene (27) determined by GC analysis.

TABLE 2

Cross metathesis reactions of allylbenzene (25) and cis-1,4-diacetoxy-2-butene (26) by catalysts $[(C_{10}H_{14})(C_3N_2H_4)(Ar)]Ru(X)[=CH—o-(O^iPr)C_6H_4]^a$

| | Catalyst | | Catalyst loading | Solvent | Temperature | Time | conversion[b] | E/Z[c] | Time | conversion[b] | E/Z[c] |
|---|---|---|---|---|---|---|---|---|---|---|---|
| Entry No. | Ar | X | mol % | — | °C. | min | % | — | min | % | — |
| 6 | 19a | Mes | $^t$BuCOO | 5.0 | C$_6$H$_6$ | 70 | 30 | 32.5 | 0.13 | 120 | 36.4 | 0.12 |
| 7 | 19a | Mes | $^t$BuCOO | 5.0 | THF | reflux | 240 | 59.5 | 0.19 | — | — | — |
| 8 | 19a | Mes | $^t$BuCOO | 5.0 | THF/H$_2$O[d] | reflux | 240 | 60.9 | 0.13 | — | — | — |
| 9 | 19a | Mes | $^t$BuCOO | 5.0 | THF/H$_2$O[e] | reflux | 240 | 64.4 | 0.14 | — | — | — |
| 10 | 19b | 2,6-Me$_2$C$_6$H$_3$ | $^t$BuCOO | 5.0 | C$_6$H$_6$ | 70 | 30 | 1.8 | 0.13 | 120 | 5.5 | 0.09 |
| 11 | 19c | 2-MeC$_{10}$H$_6$ | $^t$BuCOO | 5.0 | C$_6$H$_6$ | 70 | 30 | 1.3 | 0.12 | 120 | 2.6 | 0.11 |
| 12 | 20a | Mes | Cl | 5.0[f] | C$_6$H$_6$ | 70 | 30 | 9.7 | 2.34 | 120 | 11.0 | 2.30 |
| 13 | 20b | Mes | I | 5.0 | C$_6$H$_6$ | 70 | 60 | 0.7 | 0.23 | 120 | 1.0 | 0.43 |
| 14 | 21a | Mes | O(2,6-$^i$Pr$_2$)C$_6$H$_3$ | 5.0 | C$_6$H$_6$ | 70 | 30 | 12.3 | 0.12 | 120 | 39.5 | 0.13 |
| 15 | 21a | Mes | O(2,6-$^i$Pr$_2$)C$_6$H$_3$ | 5.0 | THF | reflux | 240 | 50.9 | 0.16 | — | — | — |
| 16 | 21b | Mes | OC$_6$Cl$_5$ | 5.0 | C$_6$H$_6$ | 70 | 120 | 0.7 | 0.16 | 480 | 2.2 | 0.21 |

TABLE 2-continued

Cross metathesis reactions of allylbenzene (25) and cis-1,4-diacetoxy-2-butene (26) by catalysts
$[(C_{10}H_{14})(C_3N_2H_4)(Ar)]Ru(X)[=CH-o-(O^iPr)C_6H_4]^a$

| Entry No. | Catalyst Ar | X | Catalyst loading mol % | Solvent — | Temperature ° C. | Time min | conversion[b] % | E/Z[c] — | Time min | conversion[b] % | E/Z[c] — |
|---|---|---|---|---|---|---|---|---|---|---|---|
| 17 | 22 | Mes | SO$_3$Mes | 5.0 | C$_6$H$_6$ | 70 | 30 | 1.6 | 0.69 | 120 | 1.7 | 0.65 |
| 18 | 22 | Mes | SO$_3$Mes | 5.0 | Et$_2$O | reflux | 240 | 8.5 | 0.85 | — | — | — |

[a]All reactions were carried out using 0.20 mmol of allylbenzene (25), 0.40 mmol of cis-1,4-diacetoxy-2-butene (26), 0.10 mmol of tridecane (internal standard for GC analysis) and 0.010 mmol of catalyst in 1.0 ml of solvent.
[b]Conversion of allylbenzene (25) to 1-acetoxy-4-phenyl-2-butene (27) determined by GC analysis.
[c]Molar ratio of E isomer and Z isomer of 1-acetoxy-4-phenyl-2-butene (27) determined by GC analysis.
[d]THF:H$_2$O = 9:1.
[e]THF:H$_2$O = 5:5.
[f]Contained 0.8 equivalent of pivalic acid.

TABLE 3

Cross metathesis reactions of allylbenzene (25) and cis-1,4-diacetoxy-2-butene (26) by Grubbs' catalysts[a]

| Entry | Catalyst No. | Catalyst loading mol % | Solvent — | Temperature ° C. | Time min | conversion[b] % | E/Z[c] — | Time min | conversion[b] % | E/Z[c] — |
|---|---|---|---|---|---|---|---|---|---|---|
| 19 | 24a | 2.5 | C$_6$H$_6$ | 23 | 10 | 60.4 | 4.44 | 60 | 78.8 | 9.02 |
| 20 | 24d | 2.5 | C$_6$H$_6$ | 23 | 10 | 73.4 | 5.18 | 60 | 79.6 | 9.93 |
| 21 | 1 | 2.5 | C$_6$H$_6$ | 23 | 30 | 13.0 | 4.12 | 120 | 40.7 | 3.93 |
| 22 | 2 | 2.5 | C$_6$H$_6$ | 23 | 30 | 16.6 | 4.00 | 120 | 31.3 | 3.87 |
| 23 | 3 | 2.5 | C$_6$H$_6$ | 23 | 1 | 8.1 | 2.95 | 30 | 67.3 | 9.63 |
| 24 | 4 | 2.5 | C$_6$H$_6$ | 23 | 1 | 69.7 | 10.55 | 30 | 66.3 | 10.66 |
| 25 | 10 | 2.5 | C$_6$H$_6$ | 23 | 1 | 60.0 | 3.67 | 30 | 83.9 | 9.11 |
| 26 | 18a | 2.5 | C$_6$H$_6$ | 23 | 1 | 0.15 | 3.10 | 30 | 0.23 | 2.90 |

[a]All reactions were carried out using 0.20 mmol of allylbenzene (25), 0.40 mmol of cis-1,4-diacetoxy-2-butene (26), 0.10 mmol of tridecane (internal standard for GC analysis) and 0.005 mmol of catalyst in 1.0 ml of solvent.
[b]Conversion of allylbenzene (25) to 1-acetoxy-4-phenyl-2-butene (27) determined by GC analysis.
[c]Molar ratio of E isomer and Z Isomer of 1-acetoxy-4-phenyl-2-butene (27) determined by GC analysis.

The metallacycle catalysts having carboxylate ligands {[2-(CH$_2$)-4,6-Me$_2$(C$_6$H$_2$)](C$_3$N$_2$H$_4$)(Mes)}-Ru(OCOR)[=CH-o-(O$^i$Pr)C$_6$H$_4$](R=$^t$Bu (7a), PhMe$_2$C (7b), Ph$_2$MeC (7c), Ph$_3$C (7d)) showed much lower E/Z ratios of 27 (E/Z=1.4-2.3 at ca 60% conversion (Entry 1-4 in Table 1) compared to typical Grubbs' 1st and 2nd generation catalysts (1-4) (Entry 21-24 in Table 3). On the other hand, non-chelated catalysts (H$_2$IMes)RuCl(OCOR)[=CH-o-(O$^i$Pr)C$_6$H$_4$](R=$^t$Bu (24a), Ph$_3$C (24d)), which also have carboxylate ligands, showed very similar E/Z ratios of 27 (Entry 19 and 20 in Table 3) compared to the Grubbs' 2nd generation catalysts (3 and 4, Entry 23 and 24 in Table 3). Thus, the enhanced Z selectivity of 7a-d is derived from their chelated structures.

{[2-(CH$_2$)-4,6-Me$_2$(C$_6$H$_2$)](C$_3$N$_2$H$_4$)(Dipp)}Ru(OCO$^t$Bu)[=CH-o-(O$^i$Pr)C$_6$H$_4$] (11) with the bulkier diisopropylphenyl group showed increased Z selectivity compared to 7a.

The catalysts with chelates containing the adamantyl group [(C$_{10}$H$_{14}$)(C$^3$N$^2$H$^4$)(R)]Ru(OCO$^t$Bu)-[=CH-o-(O$^i$Pr)C$_6$H$_4$](R=Mes (19a), 2,6-(CH$_3$)$_2$C$_6$H$_3$ (19b), 2-(CH$_3$)C$_{10}$H$_6$ (19c)) showed very high Z selectivity in the studied CM reaction (Entry 6, 10 and 11 in Table 2). E/Z ratios of 27 by these catalysts, which were 0.09-0.12 (ca 90% Z isomer) in 120 min, were the lowest among those achieved by ruthenium based olefin metathesis catalysts.

Ligand substituted catalyst [(C$_{10}$H$_{14}$)(C$_3$N$_2$H$_4$)(Mes)]RuX[=CH-o-(O$^i$Pr)C$_6$H$_4$](X=Cl (20a), I (20b), O(2,6-$^i$Pr$_2$C$_6$H$_3$) (21a), O(C$_6$Cl$_5$) (21b), SO$_3$Mes (22)) also showed moderate to excellent Z selectivity in the CM reaction (Entry 12-14, 16, 17 in Table 2). When compared to 7a, 21a gave 27 with similar E/Z ratio and better conversion (Entry 14 in Table 2).

Reaction conditions also affected conversion and stereoselectivity. When the reactions were carried out at reflux temperatures, improved conversions were observed (Entry 7, 15, 18 in Table 2). In addition, when a mixture of THF and water was used as solvent under reflux, higher conversion and lower E/Z ratio were achieved than under THF reflux (Entry 8, 9 in Table 2). These results implied not only that water could optimize reaction conditions but also that the chelate catalysts mentioned above are tolerant towards water in organic solvent. Thus, dry solvent is not necessary for these catalysts. This feature enables easy use of the catalysts in common organic synthesis and polymer synthesis.

Example 10

Comparative Results for the Self-metathesis of Allylbenzene with Catalysts 4, 7a, 11 and 19a Selected data of metathesis homo-coupling of allylbenzene (25) yielding 1,4-diphenyl-2-butene (28) (Scheme 15) are summarized in Tables 4 and 5.

Scheme 15

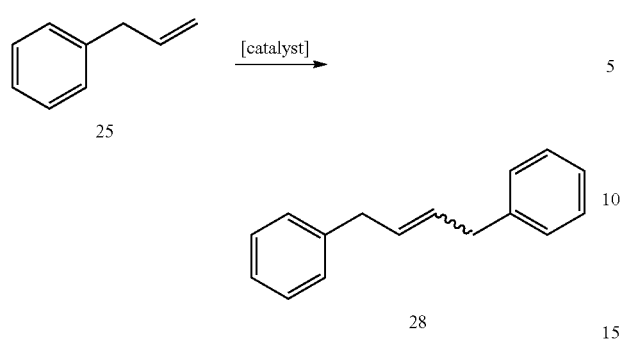

TABLE 4

Metathesis homocoupling of allylbenzene (25) by catalysts [(R)(C$_3$N$_2$H$_4$)(Ar)]Ru(OCO$^t$Bu)[=CH—o-(O$^i$Pr)C$_6$H$_4$]$^a$

| Entry | Catalyst No. | R | Ar | Catalyst loading mol % | Solvent | Temperature °C. | Time min | conversion$^b$ % | E/Z$^c$ | Time min | conversion$^b$ % | E/Z$^c$ |
|---|---|---|---|---|---|---|---|---|---|---|---|---|
| 27 | 7a | Mes$^d$ | Mes | 2.5 | C$_6$H$_6$ | 23 | 30 | 36.3 | 1.09 | 120 | 41.0 | 1.37 |
| 28 | 11 | Mes$^d$ | Dipp | 2.5 | C$_6$H$_6$ | 23 | 30 | 25.7 | 0.78 | 120 | 37.2 | 1.14 |
| 29 | 19a | Adm$^e$ | Mes | 2.5 | C$_6$H$_6$ | 70 | 30 | 51.8 | 0.04 | 120 | 65.3 | 0.17 |

$^a$All reactions were carried out using 0.20 mmol of allylbenzene (25), 0.10 mmol of tridecane (internal standard for GC analysis) and 0.005 mmol of catalyst in 1.0 ml of solvent.
$^b$Conversion of allylbenzene (25) to 1,4-diphenyl-2-butene (28) determined by GC analysis.
$^c$Molar ratio of E isomer and Z isomer of 1,4-diphenyl-2-butene (28) determined by GC analysis.
$^d$[2-(CH$_2$)-4,6-Me$_2$(C$_6$H$_2$)] connecting NHC and ruthenium.
$^e$(C$_{10}$H$_{14}$) connecting NHC and ruthenium.

TABLE 5

Metathesis homocoupling of allylbenzene (25) by Grubbs' catalyst$^a$

| Entry | Catalyst No. | Catalyst loading mol % | Solvent | Temperature °C. | Time min | conversion$^b$ % | E/Z$^c$ | Time min | conversion$^b$ % | E/Z$^c$ |
|---|---|---|---|---|---|---|---|---|---|---|
| 30 | 4 | 2.5 | C$_6$H$_6$ | 23 | 1 | 29.0 | 5.88 | 30 | 27.6 | 5.43 |

$^a$Reaction was carried out using 0.20 mmol of allylbenzene (25), 0.10 mmol of tridecane (internal standard for GC analysis) and 0.005 mmol of catalyst in 1.0 ml of solvent.
$^b$Conversion of allylbenzene (25) to 1,4-diphenyl-2-butene (28) determined by GC analysis.
$^c$Molar ratio of E isomer and Z isomer of 1,4-diphenyl-2-butene (28) determined by GC analysis.

Compared to typical Grubbs' catalyst (H$_2$IMes)RuCl$_2$[=CH-o-(O$^i$Pr)C$_6$H$_4$] (4) (Entry 30 in Table 5), all the chelate catalysts gave much lower E/Z ratio of 28 (Entry 27-29 in Table 4) and 19a showed excellent Z selectivity of the product.

Example 11

Comparative Results for the Macrocyclic RCM of 29 with Catalysts 4, 7a, 11 and 19a Selected data of ring-closing metathesis of diene (29) yielding 14-membered lactone (30) (Scheme 16) are summarized in Table 6 and 7.

Scheme 16

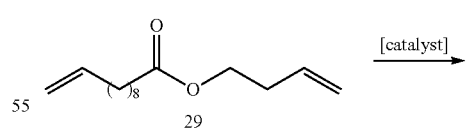

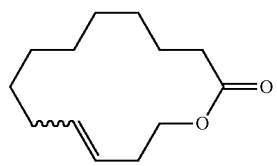

TABLE 6

Macrocyclic ring-closing metathesis by catalysts
[(R)(C₃N₂H₄)(Ar)]Ru(OCO$^t$Bu)[=CH—o-(O$^i$Pr)C₆H₄][a]

| Entry | Catalyst No. | R | Ar | Catalyst loading mol % | Solvent — | Temperature °C. | Time min | conversion[c] % | E/Z[d] — | Time min | conversion[c] % | E/Z[d] — |
|---|---|---|---|---|---|---|---|---|---|---|---|---|
| 31[a] | 7a | Mes'[e] | Mes | 5.0 | C₆H₆ | 50 | 30 | 17.4 | 1.07 | 120 | 24.2 | 1.12 |
| 32[a] | 11 | Mes'[e] | Dipp | 5.0 | C₆H₆ | 50 | 30 | 12.1 | 0.77 | 120 | 19.4 | 0.83 |
| 33[b] | 19a | Adm$^f$ | Mes | 20 | C₆H₆ | 70 | 120 | 4.6 | 0.34 | 480 | 7.5 | 0.26 |

[a]All reactions were carried out using 0.060 mmol of diene (29), 0.10 mmol of tridecane (internal standard for GC analysis) and 0.003 mmol of catalyst in 20 ml of solvent.
[b]Reaction was carried out using 0.030 mmol of diene (29), 0.10 mmol of tridecane (internal standard for GC analysis) and 0.012 mmol of catalyst in 20 ml of solvent.
[c]Conversion of diene (29) to 14-membered lactone (30) determined by GC analysis.
[d]Molar ratio of E isomer and Z isomer of 14-membered lactone (30) determined by GC analysis.
[e][2-(CH₂)-4,6-Me₂(C₆H₂)] connecting NHC and ruthenium.
[f](C₁₀H₁₄) connecting NHC and ruthenium.

TABLE 7

Macrocyclic ring-closing metathesis by Grubbs' catalyst[a]

| Entry | Catalyst No. | Catalyst loading mol % | Solvent — | Temperature °C. | Time min | conversion[b] % | E/Z[c] — | Time min | conversion[b] % | E/Z[c] — |
|---|---|---|---|---|---|---|---|---|---|---|
| 34 | 4 | 5.0 | C₆H₆ | 50 | 1 | 46.5 | 9.98 | 30 | 79.5 | 10.7 |

[a]Reaction was carried out using 0.060 mmol of diene (29), 0.10 mmol of tridecane (internal standard for GC analysis) and 0.003 mmol of catalyst in 20 ml of solvent.
[b]Conversion of diene (29) to 14-membered lactone (30) determined by GC analysis.
[c]Molar ratio of E isomer and Z isomer of 14-membered lactone (30) determined by GC analysis.

All the metallacycle catalysts showed moderate to very high Z selectivity of the product. On the other hand, 4 showed very high E selectivity of the product.

Example 12

Comparative Results for the Self-Metathesis of Methyl 10-undecenoate with Catalysts 19a and 22c

TABLE 8

Comparison of catalysts 19a and 22e for the homodimerization of methyl 10-undecenoate.

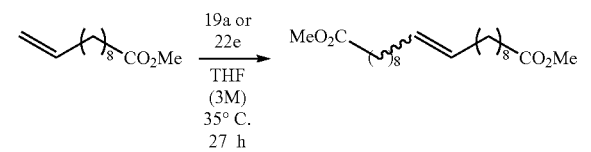

| catalyst | cat. load. (mol %) | Z. % | TON |
|---|---|---|---|
| 19a | 0.5 | 70 | 40 |
| 22e | 0.3 | >95 | 270 |

Example 13

Comparative Results for the Cross-metathesis of Allylbenzene and Cis-1,4-diacetoxy-2-butene with Catalysts 19a and 22e

TABLE 9

Cross-metathesis reaction of allylbenzene (25) and cis-1,4-diacetoxy-2-butene (26) with catalysts 19a and 22e.

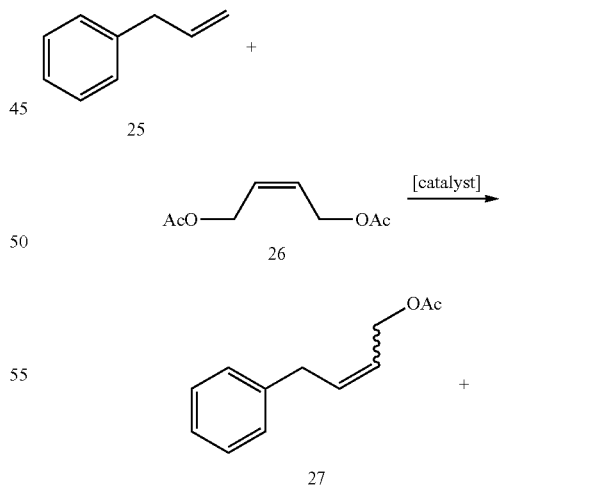

TABLE 9-continued

| catalyst | cat. load. (mol %) | temp. ° C. | time, h | 27 conv. % | 27 Z. % | 28 conv. % | 28 Z. % |
|---|---|---|---|---|---|---|---|
| 19a | 5 | 70 | 4 | 64 | 88 | 29 | 97 |
| 22e | 1 | 35 | 9 | 58 | 91 | 28 | 97 |

Example 14

Comparative Results for the Self-Metathesis of Various Terminal Olefins with Catalysts 19a and 22e

TABLE 10

Comparison of catalysts 19a and 22e for the homocoupling of various terminal olefins.

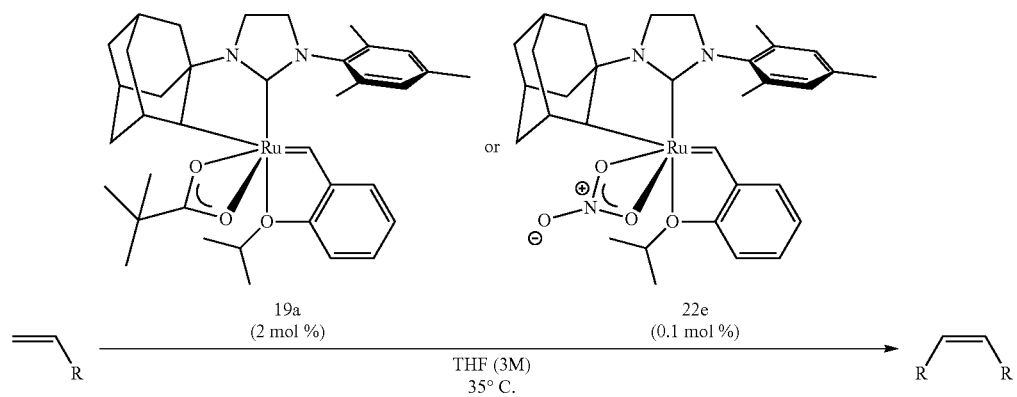

| Substrate | Catalyst | cat. loading (mol %) | Time (h) | Conv.[a] (%) | Z[a] (%) | TON[b] |
|---|---|---|---|---|---|---|
| ⫽⫽Ph | 19a | 2 | 1 | >95 | 92 | <50 |
|  | 22e | 0.1 | 9 | 88 | 86 | 880 |
| ⫽⫽TMS | 19a | 2 | 3 | >95 | >95 | <50 |
|  | 22e | 0.1 | 8 | 13 | >95 | 130 |
| ⫽⫽OAc | 19a | 2 | 4 | >95 | 89 | <50 |
|  | 22e | 0.1 | 10 | 5 | >95 | 50 |
| ⫽⫽(⫽)₅ | 19a | 2 | 3 | 73 | 69 | 37 |
|  | 22e | 0.1 | 10 | 93 | 90 | 930 |
| ⫽⫽(⫽)₈CO₂Me | 19a | 2 | 5.5 | >95 | 73 | <50 |
|  | 22e | 0.3 | 27 | 81 | >95 | 270 |
| ⫽⫽(⫽)₃OH | 19a | 2 | 1 | >95 | 72 | <50 |
|  | 22e | 0.1 | 10 | 70 | 87 | 700 |
| ⫽⫽Bpin | 19a | 2 | 4 | >95 | >95 | <50 |
|  | 22e | 0.1 | 8 | 93 | 89 | 930 |
| ⫽⫽NHPh | 19a | 2 | 2 | 70 | 71 | 35 |
|  | 22e | 0.1 | 8 | 5 | >95 | 50 |

[a]Determined by ¹H NMR spectroscopy.
[b]Conversion/Catalyst Loading.

Example 15

Alternative Procedures for the Preparation of Ru-catalyst Complex 22e

Alternative experimental procedures for the synthesis of complex 22c are presented in Schemes 17 and 18. Scheme 17 describes the synthesis starting from complex 19a and performing the ligand substitution with NH$_4$NO$_3$ in thf. Scheme 18 describes the synthesis starting from the dichloride complex 18a and performing a two-step sequence with NaOPiv in thf/MeOH and then subsequent ligand substitution with NH$_4$NO$_3$ in thf. In both cases, characterization data for 22e matches that presented previously below Scheme 12.

Scheme 17

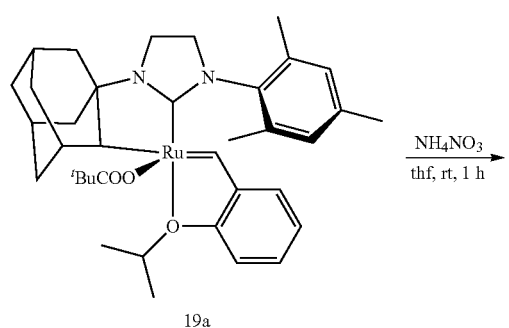

19a

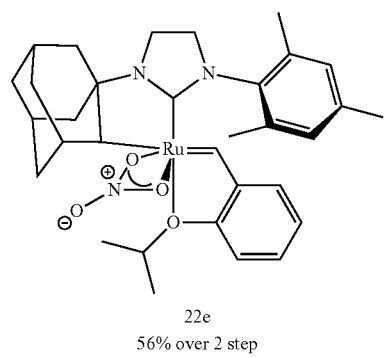

22e
56% over 2 step

Example 16

Preparation of C—H Activated Ru-catalyst Complexes 32 and 34 with Methyl Substitution on the NHC Backbone Employing a similar reaction sequences described for the synthesis of 22e in Schemes 7, 8, 9 and 17, RuCl$_2$ complexes 31 and 33 were synthesized and then converted to the C—H activated nitrate complexes 32 and 34 by the treatment with AgOPiv and subsequent anion exchange with NH$_4$NO$_3$.

Scheme 19

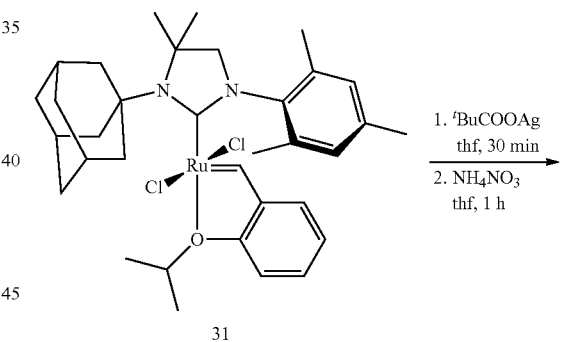

31

22e
82%

Scheme 18

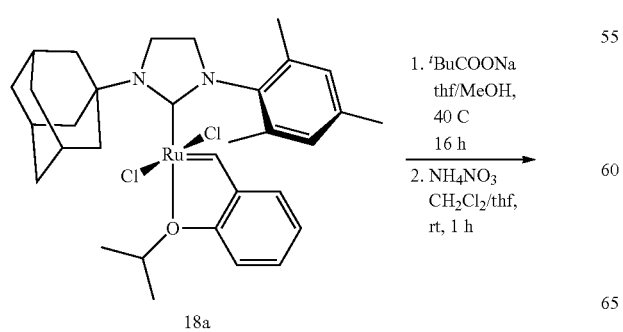

18a

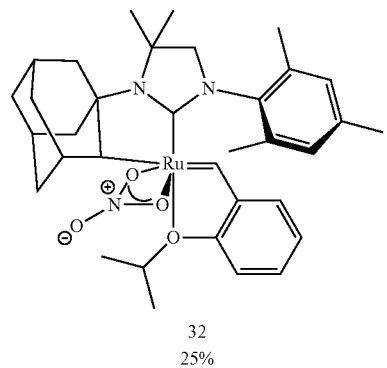

32
25%

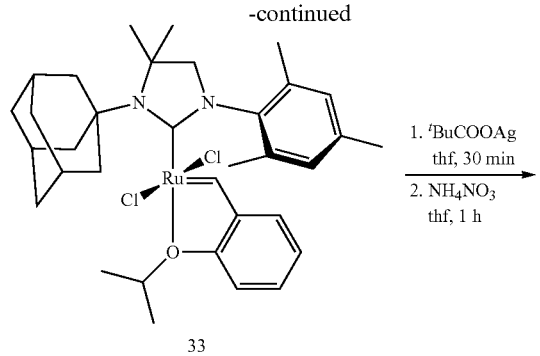

33

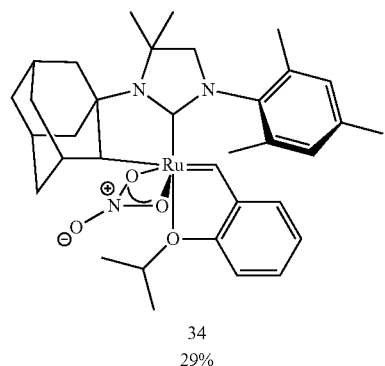

34
29%

$^1$H NMR characterization data for complex 32 is as follows:

$^1$H NMR (C$_6$D$_6$, 500 MHz) δ 15.29 (s, 1H), 7.40 (dd, 1H, J=1.5, 7.5 Hz), 7.19 (ddd, 1H, J=1.7, 7.4, 8.4 Hz), 7.00 (s, 1H), 6.84 (td, 1H, J=0.8, 7.4 Hz), 6.69 (d, 1H, J=Hz), 6.48 (d, 1H, J=8.5 Hz), 4.56 (hept, 1H, J=6.3 Hz), 4.24 (s, 1H), 3.16 (d, 1H, J=9.8 Hz), 3.05 (d, 1H, J=9.8 Hz), 2.46 (s, 3H), 2.43 (s, 3H), 2.27 (in, 1H), 2.14 (m, 1H), 2.10 (s, 3H), 1.96-2.05 (m, 2H), 1.88-1.93 (m, 1H), 1.79 (dd, 1H, J=1.7, 12.1 Hz), 1.67 (m, 1H), 1.45-1.58 (m, 3H), 1.43 (d, 3H, J=6.5 Hz), 1.12 (in, 2H), 1.07 (s, 3H), 1.00 (s, 3H), 0.96 (d, 3H, J=6.5 Hz), 0.61 (d, 1H, J=12.0 Hz).

$^1$H NMR characterization data for complex 34 is as follows:

$^1$H NMR (C$_6$D$_6$, 500 MHz) δ 15.29 (s, 1H), 7.43 (dd, 1H, J=1.6, 7.5 Hz), 7.20 (m, 1H), 7.02 (s, 1H), 6.84 (td, 1H, J=0.7, 7.4 Hz), 6.65 (s, 1H), 6.49 (d, 1H, J=8.4 Hz), 4.54 (hept, 1H, J=6.5 Hz), 4.16 (s, 1H), 3.29 (d, 1H, J=10.0 Hz), 3.10 (d, 1H, J=10.0 Hz), 2.48 (s, 3H), 2.41 (s, 3H), 2.24 (m, 2H), 2.12 (s, 3H), 2.10 (in, 2H), 2.00 (m, 1H), 1.68-1.78 (m, 2H), 1.60 (s, 1H), 1.49 (q, 2H, 0.1=12.3 Hz), 1.39 (d, 3H, J=6.0 Hz), 1.38 (in, 1H), 1.23 (s, 3H), 1.19 (s, 3H), 1.04 (m, 1H), 0.96 (d, 3H, J=6.5 Hz), 0.61 (d, 1H, J=12.0 Hz).

Example 17

Preparation of C—H Activated Ru-catalyst Complexes 36, 38 and 40 that Contain C—H Activated Moieties Different from Adamantyl Employing similar reaction procedures to that described in Schemes 8 and 9, Ru-complexes 35, 37 and 39 were prepared and then converted to C—H activated complexes 36, 38 and 40 been as outlined in Scheme 20.

Scheme 20

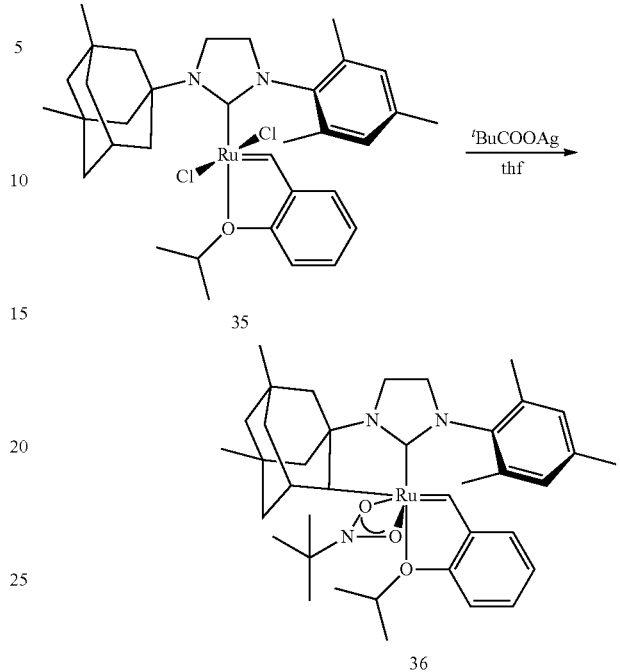

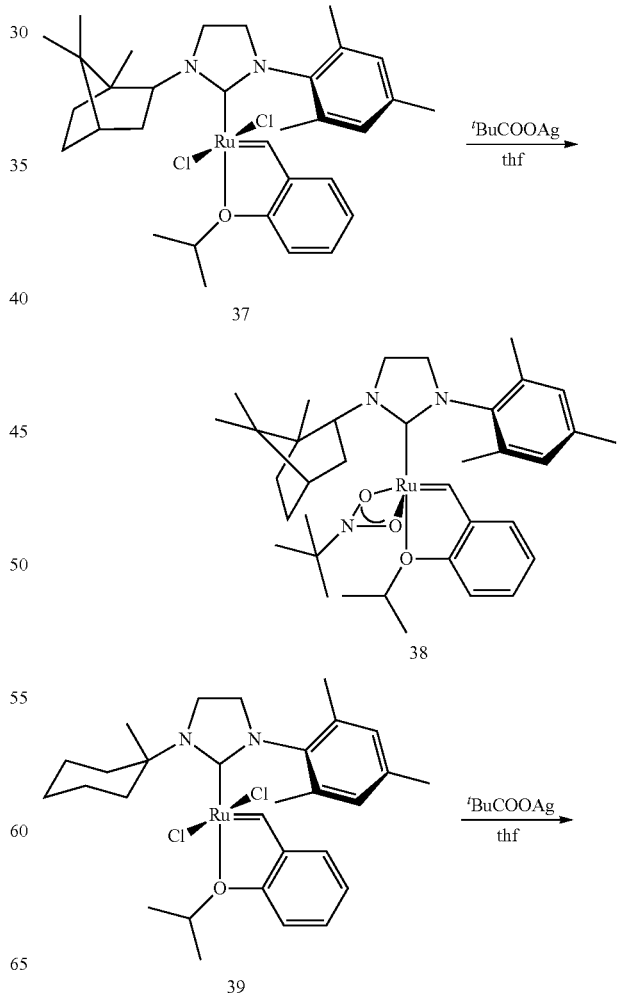

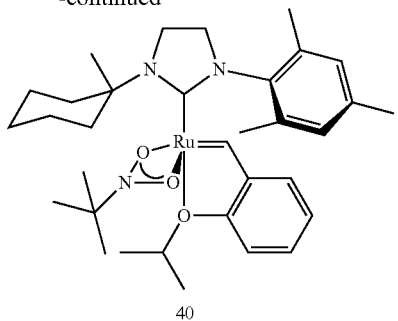

40

Representative characterization data for complex 36 is as follows:

$^1$H NMR (400 MHz, C$_6$D$_6$) δ 14.83 (s, 1H), 7.46 (dd, J=7.5, 1.7 Hz, 1H), 7.26 (t, J=1.2 Hz, 1H), 6.93 (dd, J=7.4, 0.9 Hz, 1H), 6.85-6.81 (m, 1H), 6.77-6.74 (m, 1H), 6.70 (d, J=8.3 Hz, 1H), 4.87-4.72 (m, 1H), 3.91 (s, 1H), 3.57-3.01 (m, 3H), 2.66-2.54 (m, 1H), 2.43 (s, 3H), 2.29 (s, 3H), 2.21 (s, 3H), 1.79-1.69 (m, 1H), 1.62-1.59 (m, 1H), 1.52 (d, J=6.6 Hz, 3H), 1.43-1.39 (m, 2H), 1.26 (s, 13H), 1.17 (d, J=6.2 Hz, 3H), 1.05-1.02 (m, 1H), 10.89 (s, 3H), 0.78 (dt, J=12.1, 2.8 Hz, 1H), 0.65-0.63 (m, 1H), 0.62 (s, 3H), 0.36-0.24 (m, 1H). $^{13}$C NMR (101 MHz, C$_6$D$_6$) δ 259.04, 258.78, 214.91, 154.24, 143.78, 137.96, 136.98, 136.83, 136.48, 129.90, 129.67, 125.62, 123.14, 122.79, 113.87, 74.46, 66.54, 64.09, 52.10, 51.72, 48.84, 46.63, 42.65, 41.30, 39.80, 39.10, 38.62, 33.41, 32.12, 30.77, 30.71, 28.92, 27.76, 21.64, 21.19, 21.04, 19.05, 18.97. HRMS (FAB+): Calculated—700.3178, Found—700.3181.

Example 18

Results for the Self-metathesis of Various Terminal Olefins with Catalysts 32 and 34

Selected data for the self-metathesis of various terminal olefins employing catalysts 32 and 34 are summarized in Tables 11-12: Experimental conditions were as follows: Catalyst loading: 0.1 mol %; 3M in thf; 35° C.

TABLE 11

Self-metathesis employing Catalyst 32

| Substrate | Time, h | Conv, % | Z, % |
|---|---|---|---|
| Allyl benzene | 1 | 82 | 98 |
|  | 3 | 94 | 95 |
|  | 7 | 97 | 90 |
|  | 12 | 99 | 79 |
| Methyl 10-undecenoate | 1 | 35 | 99 |
|  | 3 | 65 | 98 |
|  | 7 | 78 | 97 |
|  | 12 | 82 | 94 |
| 4-penten-1-ol | 1 | 20 | 96 |
|  | 3 | 63 | 95 |
|  | 7 | 71 | 82 |
|  | 12 | 81 | 63 |

TABLE 12

Self-metathesis with Catalyst 34

| Substrate | Time, h | Conv, % | Z, % |
|---|---|---|---|
| Allyl benzene | 1 | 72 | 98 |
|  | 3 | 92 | 95 |
|  | 7 | 97 | 72 |
|  | 12 | 98 | 53 |
| Methyl 10-undecenoate | 1 | 18 | 99 |
|  | 3 | 56 | 97 |
|  | 7 | 79 | 94 |
|  | 12 | 86 | 91 |
| 4-penten-1-ol | 1 | 6 | 95 |
|  | 3 | 55 | 88 |
|  | 7 | 73 | 78 |
|  | 12 | 85 | 76 |

Example 19

Comparative Results for the Cross-metathesis of Allylbenzene and Cis-1,4-Diacetoxy-2-Butene with Catalysts 19a, 22e and 36

TABLE 13

Comparison of catalysts 19a, 22b, 36 for cross coupling between substrates 25 and 26 for the formation of cross product 27 and homo-coupled product 28.

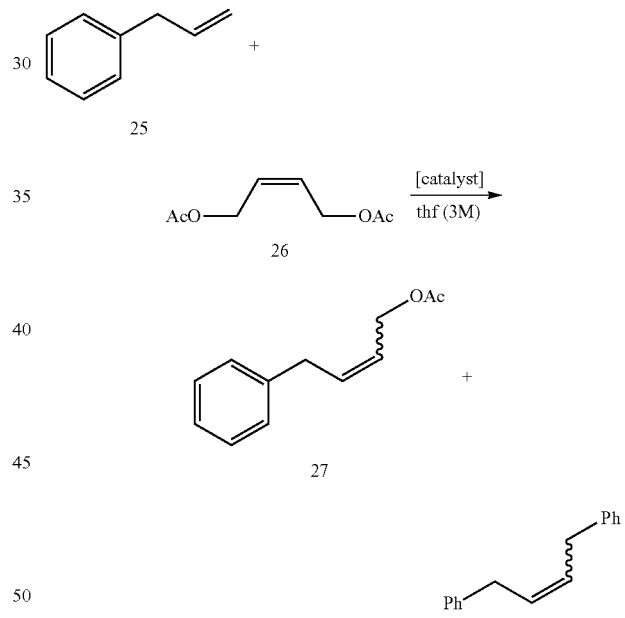

| | | | | 27 | | 28 | |
| catalyst | cat. load.. mol % | temp. ° C. | time | conv. % | Z. % | conv. % | Z. % |
|---|---|---|---|---|---|---|---|
| 19a | 5 | 35 | 9 h | 37 | 89 | 26 | 96 |
| 22b | 5 | 35 | 20 min | 11 | 77 | 12 | 88 |
|  |  |  | 30 min | 23 | 83 | 19 | 90 |
|  |  |  | 1.5 h | 36 | 82 | 26 | 91 |
|  |  |  | 3 h | 43 | 83 | 30 | 92 |
|  |  |  | 6 h | 48 | 82 | 34 | 91 |
| 36 | 5 | 35 | 5 min | 19 | 89 | 18 | 95 |
|  |  |  | 15 min | 37 | 87 | 29 | 93 |
|  |  |  | 30 min | 42 | 86 | 33 | 92 |
|  |  |  | 1.5 h | 47 | 84 | 35 | 91 |
|  |  |  | 4 h | 47 | 82 | 35 | 92 |

What is claimed is:

1. A C—H activated olefin metathesis catalyst compound, wherein the compound has the structure of formula (VIII):

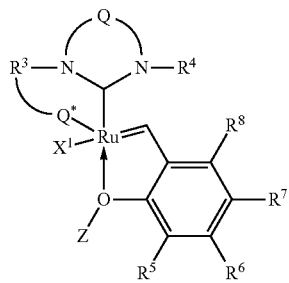

(VIII)

wherein,
Q is hydrocarbylene, or alkyl substituted hydrocarbylene;
Q* forms a carbon-Ruthenium bond with the carbon from the $R^3$ group;
$X^1$ is nitrate, or $C_1$-$C_{20}$ alkylcarboxylate;
$R^3$ is a cycloalkyl or an alkyl substituted cycloalkyl group;
$R^4$ is an alkyl substituted aryl group;
Z is alkyl; and
$R^5$, $R^6$, $R^7$ and $R^8$ are hydrogen.

2. The compound of claim 1, wherein
Q is selected from: —$CH_2$—$CH_2$—, —$C(Me)_2$— and —$CH_2$—$C(Me)_2$—; and
$R^3$ is an adamantyl or an alkyl substituted adamantyl group, or an alkyl substituted $C_3$-$C_{12}$ cycloalkyl group.

3. The compound of claim 2, wherein $R^4$ is an alkyl substituted aryl group in which both ortho ring positions are substituted.

4. The compound of claim 2, selected from

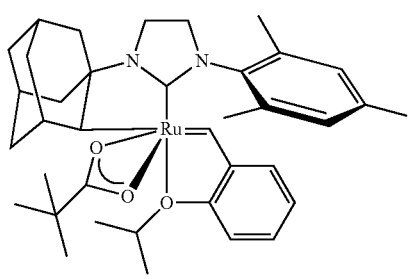

19a

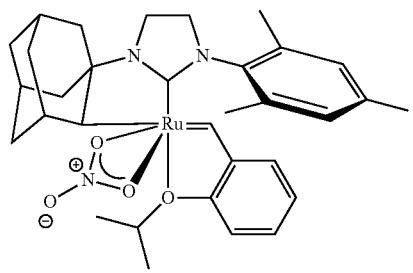

22e

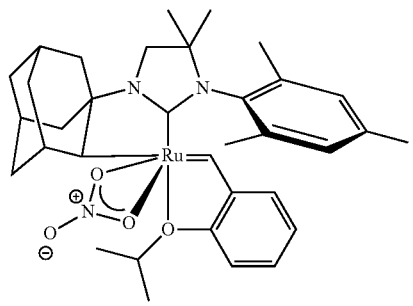

32

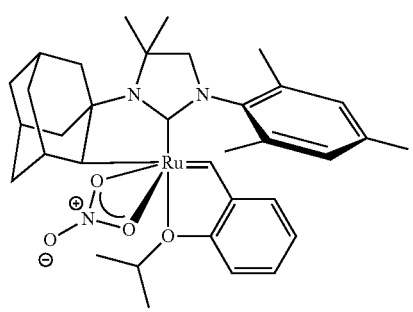

34 and

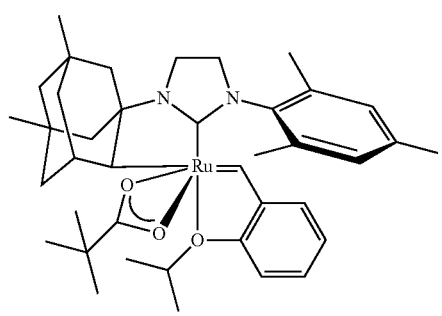

36

.

* * * * *